United States Patent
Neuhaus et al.

(10) Patent No.: US 6,891,088 B1
(45) Date of Patent: May 10, 2005

(54) TRANSGENIC PLANTS WITH A MODIFIED ACTIVITY OF A PLASTIDIAL ADP/ATP TRANSLOCATOR

(75) Inventors: Ekkehard Neuhaus, Osnabruck (DE); Torsten Moehlmann, Bunde (DE); Karl-Heinz Graeve-Kampfenkel, Mainz-Kostheim (DE); Joachim Tjaden, Osnabruck (DE)

(73) Assignee: Bayer Bioscience GmbH, Potsdam (DE)

( * ) Notice: Subject to any disclaimer, the term of this patent is extended or adjusted under 35 U.S.C. 154(b) by 0 days.

(21) Appl. No.: 09/674,768

(22) PCT Filed: May 12, 1999

(86) PCT No.: PCT/EP99/03292

§ 371 (c)(1),
(2), (4) Date: Feb. 23, 2001

(87) PCT Pub. No.: WO99/58654

PCT Pub. Date: Nov. 18, 1999

(30) Foreign Application Priority Data

May 13, 1998 (DE) .......................................... 198 21 442

(51) Int. Cl.[7] ........................ C12N 15/29; C12N 15/31; C12N 15/52; C12N 15/82; A01H 5/00
(52) U.S. Cl. .................... 800/317.2; 800/278; 800/284; 800/298; 800/320.1; 800/320.3; 435/419
(58) Field of Search ............................ 800/320.3, 278, 800/285, 286, 290, 298, 281, 284, 295, 306, 320.1, 317.2, 320.2; 536/23.1, 23.2, 23.6; 435/468, 419, 410

(56) References Cited

FOREIGN PATENT DOCUMENTS

| WO | WO9111524 | 8/1991 | |
|----|-----------|--------|---|
| WO | A1-9410320 | 5/1994 | |
| WO | WO9621737 | 7/1996 | |
| WO | WO 96/24679 | * 8/1996 | ........... C12N/15/82 |

OTHER PUBLICATIONS

Willmitzer et al., Plant Polymeric Carbohydrates, 17/1993, pp. 33–39.*
Anderson J. et al. In: The Molecular and Cell Biology of the Potato, Ch. 12, Vayda et al. eds., C.A.B. International: Wallingford, UK, 1990.*
Broun et al. Science vol. 282 Nov. 13, 1998.*
Neuhaus H.E. et al. Biochemical Journal, 1993, vol. 296, pp. 395–401.*
Tetlow I.J. et al. The Plant Cell, Mar. 2004, vol. 16; pp. 694–708.*
Ohlrogge J. et al. Biochemical Society Transactions, 2000; vol. 28, part 6, pp. 567–573.*
Mohlmann T. et al. Planta, 1994 vol. 194; pp. 492–497.*
Kampfenkel, Karlheinz et al.; FEBS Letters 374 (1995) 351–355.
Mohlmann, Torsten et al.; Planta (1994) 194:492–497.
Neuhaus, H.E. et al.; The Plant Journal (1997) 11(1), 73–82.
Schunemann, Danja, et al.; Plant Physiol. (1993) 103:131–137.
Tjaden, Joachim, et al.; The Plant Journal (1998) 16(5), 531–540.
Williamson, Lisa R., et al.; Gene, 80(1989) 269–278 Elsevier.
Neuhaus, Ekkehard H. et al.; Plant Physiol. (1993) 101: 573–578.
Mohlmann et al., Eur. J. Biochem., vol. 252, pp. 353–359 (1998).
Emmermann et al., Curr. Genet., vol. 20, pp. 405–410 (1991).
Neuhaus et al., Plant Journal, vol. 11, No. 1, pp. 73–82 (1997).
NCBI Printout—Y10821.*Solanum tuberosum*–[gi:4138582].
NCBI Printout—Z49227.A. thaliana mRNA f . . . [gi:6469339].
NCBI Printout—X94626.A. thaliana mRNA f . . . [gi:1707363].
NCBI Printout—Y10821.Solanum tuberosm–[gi:4138582], Jan. 24, 1997.
NCBI Printout—Z49227.A. thalina mRNA f–[gi: 6469339], May 5, 1995.
NCBI Printout—X94626.A.thaliana mRNA f . . . [gi:1707363], Jan. 3, 1996.
Trentmann, O et al., Eur. J. Biochem. 267, 4098–4105 (2000) "Charged amino–acid residues in transmembrane domains of the plastidic ATP/ADP transporter from *Arabidopsis* are important for transport efficiency, substrate specificity, and counter exchange properties".

* cited by examiner

Primary Examiner—Elizabeth Micelwain
Assistant Examiner—Russell Kallis
(74) Attorney, Agent, or Firm—Birch, Stewart, Kolasch & Birch, LLP

(57) ABSTRACT

Transgenic plant cells and plants are described which, compared to wildtype cells and plants, exhibit an increased yield, in particular, an increased oil and/or starch content and which preferably synthesize a modified starch. The described plants exhibit an increase or a decrease of the plastidial ADP/ATP translocator activity.

20 Claims, 8 Drawing Sheets

DC Alignment:
1 AATP1_A.T._
2 AATP2_A.t_
3 TLC_

```
        10        20        30        40        50        60
1 MEAVIQTRGLLSLPTKPIGVRSQLQPSHGLKQRLFAAKPRNLHGCLYPLTGTRNFKPLSQ  60
2 MEGLIQTRGILSLPASHR-SEKVLQPSHGLKQRLFTTN---LPALSLSLMVTRNFKPFSK  56
3 ---------MS---------------TSK----------SENY--LS-             11

70        80        90       100       110       120
1 PCMGFRFPTKREAPSSYARRRRGCWRRSCLRRSDSAAVVASRKIFGVEVATLKKIIPLGL 120
2 SHLGFRFPTRREAEDSLARRKLRRPRRKCVDEGDTAAMAVSPKIFGVEVTTLKKIVPLGL 116
3 ----------EL-----------RKIIWP-------------IEQYENKKFLPLAF     33

130       140       150       160       170       180
1 MFFCILFNYTILRDTKDVLVVTAKGSSAEIIPFLKTWVNLPMAIGFMLLYTKLSNVLSKK 180
2 MFFCILFNYTILRDTKDVLVVTAKGSSAEIIPFLKTWVNVPMAIGFMLLYTKLSNVLSKK 176
3 MMFCILLNYSTLRSIKDGFVVTDIG-T-ESISFLKTYIVLPSAVIAMIIYVKLCDILKQE  91

190       200       210       220       230       240
1 ALFYTVIVPFIIYFGGFGFVMYPLSNYIHPEALADKLLTTLGPRFMGPIAILRIWSFCLF 240
2 ALFYTVIVPFIVYFGAFGFVMYPRSNLIQPEALADKLLATLGPRFMGPLAIMRIWSFCLF 236
3 NVFYVITSFFLGYFALFAFVLYPYPDLVHPDHKTIESLSLAYPNFKWFIKIVGKWSFASF 151

250       260       270       280       290       300
1 YVMAELWGSVVVSVLFWGFANQITTVDEAKKFYPLFGIGANVALIFSGRTVKYFSNLRKN 300
2 YVMAELWGSVVVSVLFWGFANQITTVDEAKKFYPLFGLGANVALIFSGRTVKYFSNMRKN 296
3 YTIAELWGTMMLSLLFWQFANQITKIAEAKRFYSMFGLLANLALPVTSVVIGYFLHEKTQ 211

310       320       330       340       350       360
1 LGPGVDGSFV--ESHDEHCGGNGTRICLSIGGSNRYV---P-L--PTRSKNKKEKPKMGT 352
2 LGPGVDGWAVSLKAMMSIVVGMGLAICFLYWWVNRYV---P-L--PTRSKKKKVKPQMGT 350
3 I-VAEHLKFV---PLFVIMITSSFLIILTYRWMNKNVLTDPRLYDPALVKEKKTKAKLSF 267

370       380       390       400       410       420
1 MESLKFLVSSPYIRDLATLVVAYGISINLVEVTWKSKLKAQFPSPNEYSAFMGAFSTCTG 412
2 MESLKFLVSSPYIRDLATLVVAYGISINLVEVTWKSKLKSQFPSPNEYSAFMGDFSTCTG 410
3 IESLKMIFTSKYVGYIALLIIAYGVSVNLVEGVWKSKVKELYPTKEAYTIYMGQFQFYQG 327

430       440       450       460       470       480
1 VATFTMMLLSQYVFNKYGWGVAAKITPTVLLLTGVAFFSLILFGGPFA-PLVAKLGMTPL 471
2 IATFTMMLLSQYVFKKYGWGVAAKITPTVLLLTGVAFFSLILFGGPFA-PLVAKLGMTPL 469
3 WVAIAFMLIGSNILRKVSWLTAAMITPLMMFITGAAFFSFIFFDSVIAMNLTGILASSPL 387

490       500       510       520       530       540
1 LAAVYVGALQNIFSK-SAKYSLFDPCKEMAYIPLDEDTKVKGKAAIDVVCNPLGKSGGAL 530
2 LAAVYVVPPEVSSARVQVQHSSTPSAMQECLYPLDEVSKVKAKLQL-MWSATIGKSGGAL 528
3 TLAVMIGMIQNVLSK-GVKYSLFDATKNMAYIPLDKDLRVKGQAAVEVIGGRLGKSGGAI 446

550       560       570       580       590       600
1 IQQ-FMIL--SFGSLANSTPYLGMILLVIVTAWLAAAKSLEGQFNSLRLKKSLRRKWREL 587
2 IQQ-FMIL--TFGSLANSTPYLGVILLGIVTAWLAAAKSLEGPV---------------- 569
3 IQSTFFILFPVFGFI-EATPYFASIFFIIVILWIFAVKGLNKEYQVL-VNKNEK------ 498
```

TRANSGENIC PLANTS WITH A MODIFIED ACTIVITY OF A PLASTIDIAL ADP/ATP TRANSLOCATOR

This application is the national phase under 35 U.S.C. § 371 of PCT International Application No. PCT/EP99/03292 which has an International filing date of May 12, 1999, which designated the United States of America.

The present invention relates to transgenic plant cells and plants with an increased plastidial ADP/ATP translocator activity. Such cells and plants exhibit an increased yield, preferably an increased oil and/or starch content, and synthesize preferably a starch with increased amylose content.

Further, the present invention relates to transgenic plant cells and plants with a decreased ADP/ATP translocator activity. Such cells and plants synthesize a starch with decreased amylose content.

In the field of agriculture and forestry there have been permanent endeavours to provide plants with an increased yield, in particular, in order to ensure the food supply of the permanently growing world population and to guarantee the supply of regenerating raw materials. Traditionally, it has been tried to obtain high-yield plants by breeding. This, however, is time-consuming and costly. Furthermore, corresponding breeding programs have to be carried out for each plant species of interest.

Progress has been made, partly, by genetic manipulation of plants, i.e. by purposeful introduction and expression of recombinant nucleic acid molecules in plants. Approaches of that kind have the advantage that they are, in general, not limited to one plant species but can be transferred to other plant species, too.

In EP-A 0 511 979, for example, it was described that the expression of a prokaryotic asparagin synthetase in plant cells leads to an increased biomass production, amongst others. WO 96/21737 describes, for example, the increase in yield of plants by expression of de- or unregulated fructose-1,6-bisphosphatase due to increase in the rate of photosynthesis. Nevertheless, there is still a need for generally applicable methods for the improvement of the yield in plants interesting for agriculture or forestry.

Furthermore, with regard to the fact that substances contained in plants play a more and more important role as renewable sources of raw material, one of the problems in biotechnological research is the adjustment of said vegetable raw materials to the requirements of the processing industry. In order to allow for application of regenerating raw materials in as many fields as possible it is furthermore necessary to achieve a wide range of substances. Moreover, it is necessary to increase the yield of said vegetable content substances in order to increase the efficiency of the production of renewable sources of raw material from plants.

Apart from fats and proteins, oils and polysaccharides are the essential regenerating vegetable raw materials. A central role with the polysaccharides, apart from cellulose, plays starch which is one of the most important reserve substances in higher plants. Amongst those, potato and maize, in particular, are interesting plants since they are important cultivated plants for the production of starch.

The polysaccharide starch which is one of the most important reserve substances in the vegetable world is, apart from its use in the food industry, widely used as regenerating raw material for the production of industrial products.

The starch industry has a great interest in plants with increased starch content which, as a rule, means an increased dry weight. An increased dry weight increases the value of the plants processed in the starch industry (maize, potato, tapioca, wheat, barley, rice etc.) due to the increased yield of starch. In addition, plant cells or organs containing higher amounts of starch offer advantages for the processing in the food industry since they absorb less fat or frying oil and, thus, lead to "healthier" products with reduced caloric content. Said property is of great importance e.g. in the production of popcorn, corn flakes from maize or chips, crisps or potato fritters from potatoes.

For the industry processing potato starch the dry weight (starch content) is a crucial size since it determines processing costs. An increased dry weight (starch content) means, that with the same yield, the water content of the potato tuber is reduced. The reduced water content leads to reduced transport costs and to a reduction of the exact cooking period necessary in cooking.

Therefore, it seems desirable to provide plant cells and plants exhibiting an increased starch content as well as methods for the production of such plant cells and plants. Moreover, it seems desirable to provide starches whose amylose and amylopectin content meets the requirements of the processing industry. In this context, both starches with an increased amylose content and starches with a reduced amylose content are of interest since they are particularly suitable for special uses each.

Thus, the problem underlying the present invention is to provide plant cells and plants which, in comparison with corresponding non-modified wild type plant cells and wild type plants, exhibit an increased yield preferably of oil and/or starch and/or synthesize a starch with a modified amylose content.

This problem is solved by the provision of the embodiments characterized in the claims.

Thus, the present invention relates to transgenic plant cells which are genetically modified, wherein the genetic modification is the introduction of a foreign nucleic acid molecule whose presence or expression leads to an increase in the plastidial ADP/ATP translocator activity in the transgenic cells in comparison with corresponding genetically non-modified plant cells from wild type plants.

In this context, the genetic modification can be any genetic modification leading to an increase in the plastidial ADP/ATP translocator activity. One possibility, for example, is the so-called "in situ-activation", wherein the genetic modification is a change of the regulatory regions of endogenous ADP/ATP translocator genes, which leads to an increased expression of said genes. This can be achieved, for example, by means of introduction of a very strong promoter in front of the corresponding genes, e.g. by means of homologous recombination.

Further, there is the possibility to apply the method of the so-called "activation tagging" (cf. e.g. Walden et al., Plant J. (1991), 281–288; Walden et al., Plant Mol. Biol. 26 (1994), 1521–1528). Said method is based on the activation of endogenous promoters by means of enhancer elements such as the enhancer of the $^{35}$S RNA promoter of the cauliflower mosaic virus or the octopin synthase enhancer.

In a preferred embodiment the genetic modification comprises, however, the introduction of a foreign nucleic acid molecule encoding a plastidial ADP/ATP translocator into the genome of the plant cell.

The term "transgenic", therefore, means that the plant cell of the invention contains at least one foreign nucleic acid molecule encoding a plastidial ADP/ATP translocator stably intergrated in the genome, preferably a nucleic acid molecule.

The term "foreign nucleic acid molecule" preferably means a nucleic acid molecule which encodes a protein with the biological activity of a plastidial ADP/ATP translocator and either does not occur naturally in corresponding plant cells or does not occur naturally in the precise spatial order in the plant cells or which is localized at a place in the genome of the plant cell where it does not occur naturally. Preferably, the foreign nucleic acid molecule is a recombinant molecule which consists of various elements and whose combination or specific spatial arrangement does not occur naturally in plant cells. The transgenic plant cells of the invention contain at least one foreign nucleic acid molecule encoding a protein with the biological activity of a plastidial ADP/ATP translocator, wherein said nucleic acid molecule preferably is connected with regulatory DNA elements ensuring the transcription in plant cells, in particular with a promoter.

In principle, the foreign nucleic acid molecule can be any nucleic acid molecule encoding an ADP/ATP translocator which, after expression, is localized in the inner membrane of plastids. In this context, a plastidial ADP/ATP translocator is a protein catalyzing the transport of ATP into the plastids and of ADP out of the plastids. Such nucleic acid molecules are known, for example, from *Arabidopsis thaliana* (Kampfenkel et al., FEBS Lett. 374 (1995), 351–355; Genebank Acc. No. X94626 and Acc. No. Z49227) or from potato (Genebank Acc. No. Y10821). By means of said known nucleic acid molecules the person skilled in the art can isolate corresponding sequences from other organisms, particularly vegetable ones, according to standard methods, for example by heterologous screening. In particular, non-vegetable nucleic acid molecules can be used, too, which encode an ADP/ATP translocator and are connected with a targeting sequence ensuring the localisation in the inner plastid membrane. In this context, e.g. an ADP/ATP translocator is known from *Rickettsia prowazekii* (Williamson et al., Gene 80 (1989), 269–278) and from *Chlamydia trachomatis*.

In a preferred embodiment the foreign nucleic acid molecule encodes a plastidial ADP/ATP translocator form *Arabidopsis thaliana*, in particular the protein AATP1 described in Kampfenkel et al. (1995, loc. cit.).

The cells of the invention can be distinguished from naturally occurring plant cells, amongst others, in that they contain a foreign nucleic acid molecule which does not occur naturally in said cells or in that said molecule is integrated at a place in the genome of the cell where it does not normally occur, i.e. in another genomic environment. Further, said transgenic plant cells of the invention can be differentiated from naturally occurring plant cells in that they contain at least one copy of the foreign nucleic acid molecule stably integrated in their genome, optionally in addition to the copies of said molecule naturally occurring in the cells. If the nucleic acid molecule(s) introduced into the cells is/ (are) an additional copy(ies) of molecules naturally occurring in the cells, the plant cells of the invention can be differentiated from naturally occurring plant cells particularly in that said additional copy(ies) is/ (are) located at places in the genome where it (they) (do)/ does not occur naturally. This can, for example, be determined by means of a Southern blot analysis.

The plant cells of the invention can further be differentiated from naturally occurring plant cells preferably by at least one of the following features: If the nucleic acid molecule is heterologous regarding the plant cell, the transgenic plant cells exhibit transcripts of the nucleic acid molecule introduced, which can be detected by e.g. Northern blot analysis. Preferably, the plant cells of the invention contain a protein which is encoded by a nucleic acid molecule introduced. This can be detected by e.g. immunological methods, particularly by Western blot analysis.

If the nucleic acid molecule is homologue regarding the plant cell, the cells of the invention can be differentiated from naturally occurring cells, for example, due to the additional expression of the foreign nucleic acid molecules introduced. Preferably, the transgenic plant cells contain more transcripts of the foreign nucleic acid molecules. This can be detected by e.g. Northern blot analysis.

The term "genetically modified" means that the plant cell is modified in its genetic information by the introduction of a foreign nucleic acid molecule and that the presence or the expression of the foreign nucleic acid molecule leads to a phenotypic change. In this context, phenotypic change preferably means a measurable change of one or more functions of the cells. For example, the genetically modified plant cells of the invention exhibit an increase in the activity of a plastidial ADP/ATP translocator due to the presence or upon expression of the foreign nucleic acid molecule introduced.

In the context of the present invention the term "increase in the activity" means an increase of the expression of a plastidial ADP/ATP translocator gene, an increase in the amount of plastidial ADP/ATP translocator protein and/or an increase in the activity of a plastidial ADP/ATP translocator in the cells.

The increase in the expression can, for example, be determined by measurement of the amount of transcripts encoding ADP/ATP translocator, for example by means of Northern blot analysis. In this context, an increase preferably means an increase in the amount of transcripts in comparison with corresponding non-genetically modified cells by at least 10%, preferably by at least 20%, particularly by at least 50% and particularly preferred by at least 75%. The increase in the amount of ADP/ATP translocator protein can, for example, be determined by Western blot analysis. In this context, an increase preferably means an increase in the amount of ADP/ATP translocator protein in comparison with corresponding non-genetically modified cells by at least 10%, preferably by at least 20%, particularly by at least 50% and particularly preferred by at least 75%.

The activity of the plastidial ADP/ATP translocator can be determined, for example, by isolating the plastids from the corresponding tissue and determining the $V_{max}$-values of the ATP import by means of the silicone oil filtration method. The purification of various plastid types is described in e.g. Neuhaus et al. (Biochem. J. 296 (1993), 395–401). The silicone oil filtration method is described e.g. in Quick et al. (Plant Physiol. 109 (1995), 113–121).

It was surprisingly found that with plants containing said plant cells with increased activity of the plastidial ADP/ATP translocator the yield of content substances and/or biomass is increased in comparison with corresponding non-modified wild type plants. It was, for example, found that the oil content and/or the starch content in plants according to the invention is increased and/or that also the amylose content of these starches is increased in comparison with non-modified wild type plants.

In this context, the term "wild type plant" refers to plants which serve as starting material for the production of the plants described, i.e. plants of which the genetic information—apart from the genetic modification introduced—is identical to the genetic information of a plant of the invention.

The term "increased yield" means that the portion of content substances, preferably starch or oil in the plant cells of the invention is increased by at least 10%, preferably by at least 20%, more preferably by at least 30% and most preferably by at least 40% in comparison with plant cells of non-modified wild type plants.

The term "increased starch content" means that the portion of starch in plant cells according to the invention is increased by at least 10%, preferably by at least 20%, more preferably by at least 30% and most preferably by at least 40% in comparison with plant cells of non-modified wild type plants.

The determination of the starch portion is carried out according to the methods described in the appended Examples.

The term "increased amylose content" means that the amylose content of the starch synthesized in the plant cells of the invention is increased by at least 10%, preferably by at least 20%, more preferably by at least 30% and most preferably by at least 40% in comparison with plant cells of non-modified wild type plants.

The amylose content is determined by carrying out the methods described in the appended Examples.

As mentioned above, the plastidial ADP/ATP translocator is a transport protein which is localized in the inner membrane of plastids (Heidt et al, FEBS Lett. 5 (1969), 11–14; Pozueta-Romero et al., Proc. Nat. Acad. Sci. USA 88 (1991), 5769–5773; Neuhaus, Plant Physiol. 101 (1993) 573–578; Schünemann et al., Plant Physiol. 103 (1993), 131–137) and which catalyzes the transport of ATP into the plastids and of ADP out of the plastids Thus, the plastidial ADP/ATP translocator provides the stroma with cytosolic ATP. Kampfenkel et al. (FEBS Lett. 374 (1995), 351–355) were the first to isolate a cDNA encoding an ADP/ATP translocator (AATP1) from *Arabidopsis thaliana* (Neuhaus et al., Plant J. 11 (1997), 73–82) and which exhibits a great similarity (66.2% similarity) to the ADP/ATP translocator of the Gram-negative bacterium *Rickettsia prowazekii*. The AATP1-cDNA from *A. thaliana* encodes a strongly hydrophobic protein consisting of 589 amino acids which exhibits 12 potential transmembrane helices (Kampfenkel et al., FEBS Lett. 374 (1995), 351–355). Said cDNA could be functionally expressed in bakers' yeast and *E. coli*. After extraction of the protein and reconstitution in proteoliposomes an increase in the ATP transport rate could be determined (Neuhaus et al., Plant J. 11 (1997), 73–82). By means of antibodies against a peptide fragment of the AATP1 from *A. thaliana* it could be shown that the ADP/ATP translocator AATP1 is localized in the inner chloroplast envelope membrane (Neuhaus et al., Plant J. 11 (1997), 73–82).

The function of the plastidial ADP/ATP translocator for the plant metabolism could not be definitely clarified so far. Various functions have been taken into consideration, e.g. that the supply of the stroma with cytosolic ATP could have an influence on the import of proteins into the plastids, on the amino acid biosynthesis, the fatty acid metabolism or the starch metabolism (Flügge and Hinz, Eur. J. Biochem. 160 (1986), 563–570; Tetlow et al., Planta 194 (1994), 454–460; Hill and Smith, Planta 185 (1991), 91–96; Kleppinger-Sparace et al., Plant Physiol. 98 (1992), 723–727).

The fact that an increase in the activity of the plastidial ADP/ATP translocator leads to an increase in the starch content in the corresponding transgenic plants was, however, completely surprising. Just as surprising was the finding that the increase in the activity of the plastidial ADP/ATP translocator has an effect on the molecular composition of the produced starch. The starch from tubers of potato plants according to the invention, for example, exhibits an increased amylose content in comparison with starches from tubers of non-transformed potato plants.

So far, it has been assumed that the molecular properties of starch are exclusively determined by the interaction of starch-synthesizing enzymes, such as the branching enzymes (E.C. 2.4.1.18), the starch synthases (E.C. 2.4.1.21) and the ADP-glucosepyrophosphorylase (E.C. 2.7.7.27). The fact that the expression of a plastidial transport protein has an influence on the structure of the starch is, however, completely surprising.

The plant cells of the invention can be derived from any plant species, i.e. both from monocotyledonous and from dicotyledonous plants. Preferably the plant cells are from agricultural crop plants, i.e. from plants cultivated by humans for the purpose of nutrition or for technical, particularly industrial purposes. Generally preferred are plant cells from oil- and/or starch-synthesizing or oil- and/or starch-storing plants. Thus, the invention preferably relates to plant cells from starch-synthesizing or starch-storing plants such as cereals (rye, barley, oat, wheat, millet, sago etc.), rice, peas, maize, medullar pea, cassava, potato, rape, soy bean, hemp, flax, sunflower or vegetables (tomato, chicory, cucumber, salad etc.). Plant cells from potato, sunflower, soy bean, rice are preferred. Particularly preferred are plant cells from maize, wheat, rape and rice.

Furthermore, subject-matter of the invention are transgenic plants containing the transgenic plant cells described above. Said plants can be produced, for example, by regeneration from plant cells of the invention. The transgenic plants can, in principle, be plants of any species, i.e. both monocotyledonous and dicotyledonous plants. Preferably, they are useful plants i.e. plants cultivated by humans for the purpose of nutrition or for technical, particularly industrial purposes. These plants can be oil-and/or starch-synthesizing or oil- and/or starch-storing plants. The invention preferably relates to plants such as cereals (rye, barley, oat, wheat, millet, sago etc.), rice, peas, maize, medullar pea, cassava, potato, rape, soy bean, hemp, flax, sunflower or vegetables (tomato, chicory, cucumber, salad etc.). Preferred are potato, sunflower, soy bean, rice. Particularly preferred are maize, wheat, rape and rice.

As mentioned before, it was surprisingly found that in starch-storing plants containing plant cells of the invention with increased activity of the plastidial ADP/ATP translocator the starch content is increased in comparison with wild type plants and/or that also the amylose content of these starches is increased in comparison with corresponding non-modified wild type plants.

Thus, in a preferred embodiment the present invention also relates to starch-storing plants which contain the plant cells of the invention and which exhibit an increased starch content in comparison with non-modified wild type plants and/or an increased amylose content of said starch in comparison with corresponding non-modified wild type plants.

The term "starch-storing plants" comprises all plants with starch-storing tissues such as maize, wheat, rice, potato, rye, barley, oat. Rice, barley and potato are preferred. Particularly preferred are maize and wheat.

In this context, an increase in the "yield" ("increased yield"), an increase in the starch content ("increased starch content"), an increase in the amylose content ("increased amylose content") and the term "wild type plant" are used within the meaning of the definitions above and are used within the same meaning for the following embodiments of the invention, too. The term "increased yield" preferably means an increase in the production of content substances and/or biomass, in particular, if it is measured by means of fresh weight per plant.

Said increase in the yield preferably relates to parts of plants which can be harvested such as seeds, fruits, storage roots, roots, tubers, blossoms, buds, shoots, stems or wood.

According to the invention the increase in the yield is at least 3% with regard to the biomass and/or content substances in comparison with corresponding non-transformed plants of the same genotype, if said plants are cultivated under the same conditions, preferably at least 10%, more preferably at least 20% and most preferably at least 30% or even 40% in comparison with wild type plants.

Said plants according to the invention have, for example, in comparison with other plants synthesizing starch with increased amylose content such as the amylose-extender and the dull mutants from maize, the advantage that apart from an increased amylose content they exhibit no reduced but even an increased starch content.

Moreover, subject-matter of the present invention are oil-storing plants which contain the plant cells of the invention and which exhibit an increased oil content in comparison with non-modified wild type plant cells, preferably in cells of oil-storing tissue.

The term "oil-storing plants" comprises all plants able to store oil such as rape, canola, soy bean, sunflower, maize, peanut, wheat, cotton, oil palms, olive trees and avocado. Preferred are maize, wheat and soy bean. Particularly preferred are rape and canola.

The term "increased oil content" means that the oil content in plant cells of the invention is increased by at least 10%, preferably by at least 20%, more preferably by at least 30% and most preferably by at least 40% in comparison with plant cells from non-modified wild type plants.

Methods for the determination of the oil content are known to the person skilled in the art and described, for example, by Matthaeus and Bruehl, GIT Labor-Fachz. 43 (1999), 151–152, 154–155; Matthaeus, Laborpraxis 22 (1998), 52–55. The determination of the oil content may also be carried out by non-invasive near IR-spectroscopy which is an analysing method (commonly used in breeding) and was described e.g. by Schulz et al., J. Near Infrared Spectrosc. 6 (1998), A125–A130; Starret al., J. Agric. Sci. 104 (1985), 317–323.

Plants exhibiting an increased concentration of oil are of great commercial interest. Maize plants, for example, whose grains exhibit a high level of starch but also an increased content of the side product oil are of great interest for the wet milling industry since the side product is of high value. The feed-stuff industry is also interested in feeding plants with increased oil content since such plants have an increased nutritious value. For the oil plants-processing industry an increase of the oil content means an increase of the efficiency of the oil extracting process.

The present invention further relates to a method for the production of transgenic plants which, compared to wild type plants, exhibit an increased yield, wherein
(a) a plant cell is genetically modified by means of introduction of a foreign nucleic acid molecule and the genetic modification leads to an increase of the activity of a plastidial ADP/ATP translocator; and
(b) a plant is regenerated from the cell; and optionally
(c) further plants are produced from the plant according to (b).

The present invention further relates to a method for the production of transgenic plants which, compared to wild type plants, exhibit an increased starch content and/or whose starch exhibits an increased amylose content in comparison with corresponding wild type plants, wherein
(a) a plant cell is genetically modified by means of introduction of a foreign nucleic acid molecule and the genetic modification leads to an increase of the activity of a plastidial ADP/ATP translocator; and
(b) a plant is regenerated from the cell; and optionally
(c) further plants are produced from the plant according to (b).

Moreover, subject-matter of the present invention is a method for the production of transgenic plants which, compared to wild type plants, exhibit an increased oil content, wherein
(a) a plant cell is genetically modified by means of introduction of a foreign nucleic acid molecule and the genetic modification leads to an increase of the activity of a plastidial ADP/ATP translocator; and
(b) a plant is regenerated from the cell; and optionally
(c) further plants are produced from the plant according to (b).

For the modification introduced into the plant cell according to step (a) the same applies as has been discussed above regarding the plant cells and plants of the invention.

The regeneration of plants according to step (b) can be carried out according to methods known to the person skilled in the art.

The generation of further plants according to step (c) of the methods of the invention can be achieved e.g. by vegetative propagation (for example via cuttings, tubers or via callus culture and regeneration of whole plants) or by sexual reproduction. Preferably, sexual reproduction takes place in a controlled manner, i.e. selected plants with specific properties are crossed with each other and propagated.

The present invention also relates to the plants obtainable by the method of the invention.

The present invention also relates to propagation material of plants according to the invention as well as of the transgenic plants produced according to the methods of the invention which contains genetically modified cells of the invention. In this context, the term propagation material comprises those components of the plant which are suitable for the generation of descendants by means of a vegetative or sexual way. Suitable for vegetative propagation are, for example, cuttings, callus cultures, rhizomes or tubers. Other propagation material comprises, for example, fruit, seeds, seedlings, protoplasts, cell cultures, etc. Preferably, propagation material are tubers, particularly preferred seeds.

The present invention further relates to the use of nucleic acid molecules encoding a plastidial ADP/ATP translocator for the production of transgenic plants with an increased yield in comparison with wild type plants.

The present invention further relates to the use of nucleic acid molecules encoding a plastidial ADP/ATP translocator for the production of plants which, in comparison with wild type plants, have an increased starch content in the starch-synthesizing and/or—storing tissue, or for the production of plants synthesizing a starch which, compared to starch from wild type plants, exhibits an increased amylose content. The nucleic acid molecules mentioned above in connection with the cells of the invention are preferably used.

The present invention further relates to the use of nucleic acid molecules encoding a plastidial ADP/ATP translocator for the production of transgenic plants which, in comparison with wild type plants, have an increased oil content.

The present invention further relates to transgenic plant cells which are genetically modified, wherein the genetic modification leads to the decrease of the activity of a plastidial ADP/ATP translocator present endogenously in the plant cell, compared to non-genetically modified plant cells of corresponding wild type plants.

The term "transgenic", as used herein, means that the plant cells of the invention deviate in their genetic information from corresponding non-modified plant cells due to a genetic modification, particularly the introduction of a foreign nucleic acid molecule.

In this context, the term "genetically modified" means that the plant cell is modified in its genetic information due to the introduction of a foreign nucleic acid molecule and that the presence or the expression of the foreign nucleic acid molecule leads to a phenotypic change. Phenotypic change preferably means a measurable change of one or more functions of the cell. For example, genetically modified plant cells of the invention exhibit a decrease of the activity of a plastidial ADP/ATP translocator.

The production of said plant cells of the invention with a decreased activity of an ADP/ATP translocator can be achieved by various methods known to the person skilled in the art, e.g. by methods leading to an inhibition of the expression of endogenous genes encoding a plastidial ADP/ATP translocator. Such methods include, for example, the expression of a corresponding antisense-RNA, the expression of a sense-RNA for achieving a cosuppression effect, the expression of a correspondingly constructed ribozyme which specifically cleaves transcripts encoding an ADP/ATP translocator or the so-called "in-vivo mutagenesis".

For the reduction of the activity of an ADP/ATP translocator in the cells of the invention preferably an antisense-RNA is expressed.

For the expression either a DNA molecule can be used comprising the whole sequence encoding a ADP/ATP translocator including flanking sequences that are possibly present or DNA molecules comprising only parts of the coding sequence, wherein these parts have to be long enough to lead to an antisense-effect in the cells. In general, sequences can be used up to a minimum length of 15 bp, preferably a length of 100–500 bp, for an efficient antisense-inhibition, particularly, sequences with a length of more than 500 bp. DNA molecules shorter than 5000 bp are commonly used, preferably sequences shorter than 2500 bp.

It is also possible to use DNA sequences which have a high degree of homology to the sequences which occur endogenously in the plant cell and which encode a plastidial ADP/ATP translocator. The minimal homology should be higher than approximately 65%. The use of sequences with homologies between 95 and 100% is to be preferred.

Alternatively, the reduction of the ADP/ATP translocator activity in the plant cells of the invention can also be accomplished by means of a co-suppression effect. The method is known to the person skilled in the art and is described, for example, in Jorgensen (Trends Biotechnol. 8 (1990), 340–344), Niebel et al. (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al. (Mol. Gen. Genet. 248 (1995), 311–317), de Borne et al. (Mol. Gen. Genet. 243 (1994), 613–621) and other sources.

The expression of ribozymes for the reduction of the activity of specific proteins in cells is also known to the person skilled in the art and is described, for example, in EP-B1 0 321 201. The expression of ribozymes in plant cells was described, for example, in Feyter et al. (Mol. Gen. Genet. 250 (1996), 329–338).

Moreover, the reduction of the ADP/ATP translocator activity in the plant cells of the invention can also be achieved by means of the so-called "in vivo mutagenesis", wherein a hybrid RNA-DNA-oligonucleotide ("chimeroplast") is introduced into cells by means of transformation of cells (Kipp, P. B. et al., Poster Session at the "5$^{th}$ International Congress of Plant Molecular Biology, 21–27. September 1997, Singapore; R. A. Dixon and C. J. Arntzen, Meeting report on "Metabolic Engineering in Transgenic Plants", Keystone Symposia, Copper Mountain, Colo., USA, TIBTECH 15 (1997), 441–447; international patent application WO. 95/15972; Kren et al., Hepatology 25 (1997), 1462–1468; Cole-Strauss et al., Science 273 (1996), 1386–1389).

A part of the DNA component of the RNA-DNA-oligonucleotide is homologous to a nucleic acid sequence of an endogenous ADP/ATP translocator but, compared to the nucleic acid sequence of the endogenous ADP/ATP translocator, exhibits a mutation or contains a heterologous region which is enclosed by the homologous regions.

By means of base pairing of the homologous regions of the RNA-DNA-oligonucleotide and the endogenous nucleic acid molecule followed by homologous recombination, the mutation or heterologous region contained in the DNA component of the RNA-DNA-oligonucleotide can be transferred into the genome of a plant cell. This leads to a decrease of the activity of the plastidial ADP/ATP translocator.

Thus, subject-matter of the present invention particularly are transgenic plant cells, (a) containing a DNA molecule which can lead to the synthesis of an antisense RNA causing a decrease of the expression of endogenous genes which encode a plastidial ADP/ATP translocator; and/or (b) containing a DNA molecule which can lead to the synthesis of a co-suppression-RNA causing a decrease of the expression of endogenous genes which encode a plastidial ADP/ATP translocator; and/or (c) containing a DNA molecule which can lead to the synthesis of a ribozyme which can specifically cleave transcripts of endogenous genes encoding an ADP/ATP translocator; and/or (d) which, due to an in vivo mutagenesis, exhibit a mutation or an insertion of a heterologous DNA sequence in at least one endogenous gene encoding a plastidial ADP/ATP translocator, wherein the mutation or insertion causes a decrease of the expression of the gene or the synthesis of an inactive transporter molecule.

The term "decrease of the activity" in the present invention means a decrease of the expression of endogenous genes encoding an ADP/ATP translocator, a reduction of the amount of ADP/ATP translocator protein in the cells and/or a decrease of the biological activity of the ADP/ATP translocator protein in the cells.

The decrease of the expression can be determined, for example, by measuring the amount of transcripts encoding the ADP/ATP translocator, e.g. by Northern blot analysis. A decrease preferably means a decrease of the amount of transcripts in comparison with genetically non-modified cells by at least 30%, preferably by at least 50%, more preferably by at least 70%, particularly preferred by at least 85% and most preferably by at least 95%.

The decrease of the amount of ADP/ATP translocator protein can be determined, for example, by means of Western blot analysis. A decrease preferably means a decrease of the amount of ADP/ATP translocator protein in comparison with corresponding genetically non-modified cells by at least 30%, preferably by at least 50%, more preferably by at least 70%, particularly preferred by at least 85% and most preferably by at least 95%.

Surprisingly, it was found that the starch content of plant cells which have a decreased expression and thus a decreased activity of the plastidial ADP/ATP translocator, compared to corresponding non-modified plant cells from wild type plants, is reduced and that also the amylose content of these starches, compared to corresponding non-modified plant cells from wild type plants, is reduced. The fact that the starches of the plants of the invention have a modified structure is particularly surprising since it has been assumed so far that the molecular properties of starches are exclusively determined by the interaction of starch-synthesizing enzymes such as the branching enzymes (E.C. 2.4.1.18) and the starch synthases (E.C. 2.4.1.21). It is completely surprising that the expression of a plastidial transport protein influences the structure of starch.

The term "decreased starch content" in the present invention means that the content of starch in plant cells of the invention is reduced by at least 15%, preferably by at least 30%, more preferably by at least 40% and most preferably by at least 50% in comparison with plant cells of non-modified wild type plants. The starch content is determined according to the methods described in the Examples.

The term "decreased amylose content" means that the content of amylose in the plant cells of the invention, in comparison with plant cells of non-modified wild type plants, is reduced by at least 10%, preferably by at least 20%, more preferably by at least 30% and most preferably by at least 40%. The amylose content is determined according to the methods described in the Examples.

The term "wild type plant" has the above-defined meaning.

The plant cells of the invention can derive from any plant species, i.e. both from monocotyledonous and dicotyledonous plants. Preferably these are plant cells from agricultural crop plants, i.e. from plants cultivated by humans for the purpose of nutrition or for technical, particularly industrial purposes. Preferably, thus, the invention relates to plant cells from starch-synthesizing or starch-storing plants such as cereals (rye, barley, oat, wheat, millet, sago etc.), rice, pea, maize, medullar pea, cassava, potato, tomato, rape, soy bean, hemp, flax, sunflower, cow pea and arrowroot. Particularly preferred are plant cells from potato.

Moreover, subject-matter of the invention are transgenic plants containing the transgenic plant cells described above. Said plants can be produced by regeneration from the plant cells of the invention. The transgenic plants can, in principle, be plants of any plant species, i.e. both monocotyledonous and dicotyledonous plants. Preferably they are plant cells from agricultural crop plants, i.e. from plants cultivated by humans for the purpose of nutrition or for technical, particularly industrial purposes. Preferably these are starch-synthesizing or starch-storing plants such as cereals (rye, barley, oat, wheat, millet, sago etc.), rice, pea, maize, medullar pea, cassava, potato, tomato, rape, soy bean, hemp, flax, sunflower, cow pea and arrowroot. Particularly preferred is potato.

Said plants of the invention synthesize a starch which, compared to starch from corresponding wild type plants, exhibits a reduced amylose content. The terms "reduction of the amylose content" and "wild type plants" are defined as described above.

Furthermore, the present invention also relates to a method for the production of transgenic plants whose starch, compared to starch from corresponding wild type plants, exhibits a reduced amylose content wherein (a) a plant cell is genetically modified by means of introduction of a foreign nucleic acid molecule and the genetic modification leads to a decrease of the activity of a plastidial ADP/ATP translocator present endogenously in plant cells; and (b) a plant is regenerated from the cell produced according to step (a); and optionally (c) further plants are produced from the plant produced according to step (b).

For the modification introduced into the plant cell according to step (a) the same applies as was discussed earlier in connection with the plant cells and plants of the invention.

The regeneration of plants according to step (c) can be carried out according to methods known to the person skilled in the art.

The production of further plants according to step (c) of the method of the invention can, for example, be achieved by vegetative propagation (for example via cuttings, tubers or via callus culture and regeneration of whole plants) or by sexual propagation. Preferably, sexual propagation takes place in a controlled manner, i.e. selected plants with specific properties are crossed with each other and propagated.

In a preferred embodiment the method of the invention is used for the production of transgenic potato plants.

The present invention also relates to plants obtainable by the method of the invention.

The present invention also relates to propagation material of plants according to the invention as well as of the transgenic plants produced according to the methods of the invention which contains genetically modified cells of the invention. In this context, the term propagation material comprises those components of the plant which are suitable for the generation of descendants by means of a vegetative or sexual way. Suitable for vegetative propagation are, for example, cuttings, callus cultures, rhizomes or tubers. Other propagation material comprises, for example, fruit, seeds, seedlings, protoplasts, cell cultures, etc. Preferably, propagation material are seeds, particularly preferred tubers.

Furthermore, the present invention relates to the use of nucleic acid molecules encoding a plastidial ADP/ATP translocator, of complements thereof or of parts of said molecules for the production of plants synthesizing a starch with, in comparison with starch from wild type plants, reduced amylose content. Preferably, the nucleic acid molecules mentioned above in connection with the plant cells of the invention exhibiting an increased ADP/ATP translocator activity are to be used.

A variety of techniques are at disposal for the introduction of DNA in a plant host cell. These techniques comprise the transformation of plant cells with T-DNA using *Agrobacterium tumefaciens* or *Agrobacterium rhizogenes* as transformation agent, the fusion of protoplasts, the injection, the electroporation of DNA, the introduction of the DNA via the biolistic approach and other possibilities.

The use of Agrobacteria-mediated transformation of plant cells has been analysed in detail and was described sufficiently in EP 120516; Hoekema, in: The Binary Plant Vector System Offsetdrukkerij Kanters B. V., Alblasserdam (1985), Chapter V; Fraley et al., Crit. Rev. Plant Sci. 4, 1–46 and An et al., EMBO J. 4 (1985), 277–287. For the transformation of potato, see e.g. Rocha-Sosa et al., EMBO J. 8 (1989), 29–33.

The transformation of monocotyledonous plants by means of *Agrobacterium*-based vectors was also described (Chan et al., Plant Mol. Biol. 22 (1993), 491–506; Hiei et al., Plant J. 6 (1994) 271–282; Deng et al., Science in China 33 (1990), 28–34; Wilmink et al., Plant Cell Reports 11 (1992), 76–80; May et al., Bio/Technology 13 (1995), 486–492; Connor and Domisse, Int. J. Plant Sci. 153 (1992), 550–555; Ritchie et al., Transgenic Res. 2 (1993), 252–265). An alternative system for the transformation of monocotyledonous plants is the transformation via the biolistic approach (Wan and Lemaux, Plant Physiol. 104 (1994), 37–48; Vasil et al., Bio/Technology 11 (1993), 1553–1558; Ritala et al., Plant Mol. Biol. 24 (1994), 317–325; Spencer et al., Theor. Appl. Genet. 79 (1990), 625–631), the protoplast transformation, the electroporation of partially permeabilized cells, the introduction of DNA by means of glass fibres. The transformation of maize, in particular, is described in the literature several times (see e.g. WO 95/06128, EP 0513849, EO 0465875, EP 292435; Fromm et al., Biotechnology 8 (1990), 833–844; Gordon-Kamm et al., Plant Cell 2 (1990), 603–618; Koziel et al., Biotechnology 11 (1993), 194–200; Moroc et al., Theor. Appl. Genet. 80 (1990), 721–726).

The successful transformation of other cereals has also been described, e.g. for barley (Wan and Lemaux, loc. cit., Ritala et al., loc. cit., Krens et al., Nature 296 (1982), 72–74) and for wheat (Nehra et al., Plant J. 5 (1994), 285–297).

For the expression of the nucleic acid molecules encoding an ADP/ATP translocator in sense- or antisense-orientation in plant cells said nucleic acid molecules are preferably linked with regulatory DNA elements which ensure the transcription in plant cells. Said elements include, in particular, promoters. Generally, any promoter active in plant cells is suitable.

The promoter can be chosen in such a way that the expression takes place constitutively or only in a specific tissue, at a specific point in time of the plant development or at a point in time determined by external factors. Both with regard to the plant and with regard to the nucleic acid molecule, the promoter can be homologous or heterologous.

Suitable promoters are e.g. the promoter of the 35S RNA of the cauliflower mosaic virus and the ubiquitin promoter from maize for a constitutive expression, the patatin gene promoter B33 (Rocha-Sosa et al., EMBO J. 8 (1989), 23–29) for a tuber-specific expression in potato and a promoter ensuring an expression only in photosynthetically active tissue, e.g. the ST-LS1-promoter (Stockhaus et al., Proc. Natl. Acad. Sci. USA 84 (1987), 7943–7947; Stockhaus et al., EMBO J. 8 (1989), 2445–2451) or, for an endosperm-specific expression, the HMG promoter from wheat, the USP promoter, the phaseolin promoter, promoters from zein genes from maize (Pedersen et al., Cell 29 (1982), 1015–1026; Quatroccio et al., Plant Mol. Biol. 15 (1990), 81–93), glutelin promoter (Leisy et al., Plant Mol. Biol. 14 (1990), 41–50; Zheng et al., Plant J. 4 (1993), 357–366; Yoshihara et al., FEBS Lett. 383 (1996), 213–218) or shrunken-1 promoter (Werr et al., EMBO J. 4 (1985), 1373–1380). Promoters which are activated only at a point in time determined by external factors can, however, also be used (see for example WO 9307279). In this context, promoters of heat-shock proteins allowing for a simple induction can particularly be of interest. Moreover, seed-specific promoters can be used such as the USP promoter from *Vicia faba* which ensures a seed-specific expression in *Vicia faba* and other plants (Fiedler et al., Plant Mol. Biol. 22 (1993), 669–679; Bäumlein et al., Mol. Gen. Genet. 225 (1991), 459–467).

The aforementioned embodiments with the endospecific[1] promoters are suitable, in particular, for increasing the starch content in the endosperm. In contrast thereto, the use of embryo-specific promoters is of interest, in particular, for increasing the oil content since, as a rule, oil is mainly stored in the embryo.

[1] Translator's note: should read "endosperm-specific"

Thus, preferably a promoter is used according to the present invention which ensures the expression in the embryo or in the seed. In a preferred embodiment of the invention the promoter is the globulin-1 (glb1) promoter from maize (Styer and Cantliffe, Plant Physiol. 76 (1984), 196–200). In another embodiment of the invention the embryo-specific promoter is from plants, preferably from *Cuphea lanceolata, Brassica repa* or *Brassica napus*. Particularly preferred are the promoters pCIFatB3 and pCIFatB4 (WO 95/07357). These are promoters of the genes CIFatB3 and CIFatB4, respectively, which have already successfully been used in transgenic rape for the biosynthesis of medium-chain fatty acids and, thus, have a suitable expression window for the solution of the present problem.

In another preferred embodiment the pCIGPDH promoter (WO 95/06733), the napin (described, for example, by Kridl, Seed Sci. Res. 1 (1991), 209–219; Ellerstrom et al., Plant Mol. Biol. 32 (1996), 1019–1027; Stalberg et al., Planta 199 (1996), 515–519) or the oleosin promoter (described, for example, by Keddie, Plant Mol. Biol 24 (1994), 327–340; Plant et al., Plant Mol. Biol. 25 (1994), 193–205) is used.

Moreover, a termination sequence can be present which serves the correct termination of the transcription and the addition of a poly-A-tail to the transcript regarded as having a function in stabilizing the transcripts. Said elements are described in the literature (see, e.g., Gielen et al., EMBO J. 8 (1989), 23–29) and are interchangeable as desired.

The transgenic plant cells and plants of the invention synthesize, preferably due to the increase or decrease of the activity of a plastidial ADP/ATP translocator, a starch which, compared to synthesized starch in wild type plants, is modified in its physic chemical properties, in particular the amylose/amylopectin ratio. In particular, said starch can, compared to wild type starch, be modified with regard to the viscosity and/or the gel formation properties of glues of said starch.

Thus, the present invention relates to methods for the production of a modified starch comprising the step of extraction of the starch from one of the above-described plants and/or from starch-storing parts of said plant. Preferably, said method comprises also the step of harvesting the cultivated plants and/or starch-storing parts of said plants before the extraction of starch and further, particularly preferred, the step of cultivating the plants of the invention before harvesting. Methods for the extraction of the starch from plants or the starch-storing parts of plants are known to the person skilled in the art. Moreover, methods for the extraction of the starch from various other starch-storing plants are described, e.g. in "Starch: Chemistry and Technology (eds.: Whistler, BeMiller and Paschall (1994), $2^{ed}$ edition, Academic Press Inc. London Ltd; ISBN 0-12-746270-8; see e.g. chapter XII, page 412–468: maize and sorghum starch: production; by Watson; chapter XIII, page 469–479: starches from tapioca, arrowroot and sago: production; by Corbishley and Miller; chapter XIV, page 491–506: starch from wheat: production, modification and uses; by Knight and Oson; and chapter XVI, page 507 to 528: starch from rice: production and uses; by Rohmer and Klem; starch from maize: Eckhoff et al., Cereal Chem. 73 (1996) 54–57, the extraction of starch from maize to industrial standard is usually achieved by so-called 'wet milling'). Appliances usually used for methods for the extraction of starch from plant material are separators, decanters, hydrocyclones, spray dryers and fluidized bed dryers.

Furthermore, subject-matter of the present invention is starch obtainable from the transgenic plant cells, plants and propagation material of the invention and starch obtainable by the method of the invention described above.

The starches of the invention can be modified according to methods known to the person skilled in the art and are suitable for various uses in the foodstuff or non-foodstuff industry in unmodified or modified form.

In principle, possibilities of use can be divided into two large areas. One area comprises hydrolysis products of the starch, mainly glucose and glucan building blocks obtained via enzymatic or chemical methods. They serve as starting material for further chemical modifications and processes such as fermentation. For a reduction of costs the simplicity and inexpensive carrying out of a hydrolysis method can be of importance. At present, the method is essentially enzymatic with use of amyloglucosidase. It would be possible to save costs by reducing use of enzymes. This could be achieved by changing the structure of the starch, e.g. surface enlargement of the grain, easier digestibility due to low branching degree or a steric structure limiting the accessibility for the enzymes used.

The other area where starch is used as so-called native starch due to its polymeric structure can be subdivided into two further fields of application:

1. Use in Foodstuffs

Starch is a classic additive for various foodstuffs, in which it essentially serves the purpose of binding aqueous additives and/or causes an increased viscosity or an increased gel formation. Important characteristic properties are flowing and sorption behaviour, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

2. Use in Non-Foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

2.1 Paper and Cardboard Industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textiles and Textile Care Products

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behaviour for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building Industry

Furthermore, starch may be used as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilisation

Furthermore, the starch is advantageous for the production of means for ground stabilisation used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use in Plant Protectives and Fertilizers

Another field of application is the use of starch in plant protectives for the modification of the specific properties of these preparations. For instance, starch is used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, Medicine and Cosmetics Industry

Starch may also be used in the fields of drugs, medicine and in the cosmetics industry. In the pharmaceutical industry, starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medical lubricating and vulnerary dusting powders are further fields of application. In the field of cosmetics, the starch may for example be used as a carrier of powder additives, such as scents and salicylic acid. A relatively extensive field of application for the starch is toothpaste.

2.8 Starch as an Additive in Coal and Briquettes

Starch can also be used as an additive in coal and briquettes. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, starch is suitable as a binding agent since adding it to coal and briquette can considerably reduce the emission of toxic substances.

2.9 Processing of Ore and Coal Slurry

Furthermore, starch may be used as a flocculant in the processing of ore and coal slurry.

2.10 Additive for Casting Materials

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfil more prerequisites for the production process, such as dispersability in cold water, rehydratisability, good mixability in sand and high capability of binding water.

2.11 Rubber Industry

In the rubber industry starch may be used for improving the technical and optical quality. Reasons for this are improved surface gloss, grip and appearance. For this purpose, starch is dispersed on the sticky rubberised surfaces of rubber substances before the cold vulcanization. It may also be used for improving the printability of rubber.

2.12 Production of Leather Substitutes

Another field of application for modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behaviour, improved antiblock behaviour as well as improved printability with aqueous dyes.

Another possibility is the use of the starch in polyurethane foams. Due to the adaptation of starch derivatives as well as due to the optimisation of processing techniques, it is possible to specifically control the reaction between synthetic polymers and the hydroxy groups of the starch. The results are polyurethane films having the following property profiles due to the use of starch: a reduced coefficient of thermal expansion, decreased shrinking behaviour, improved pressure/tension behaviour, increased water vapour permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterised by an improved binding and retaining capability of up to 1000 g water per g starch at a high viscosity. These super absorbers are used mainly in the hygiene field, e.g. in products such as nappies and sheets, as well as in the agricultural sector, e.g. in seed pellets.

What is decisive for the use of the novel starch modified by recombinant DNA techniques are, on the one hand, structure, water content, protein content, lipid content, fiber content, ashes/phosphate content, amylose/amylopectin ratio, distribution of the relative molar mass, branching degree, granule size and shape as well as crystallization, and on the other hand, the properties resulting in the following features: flow and sorption behaviour, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known. These are particularly modifications by means of heat treatment
acid treatment
oxidation and
esterification leading to the formation of phosphate, nitrate, sulfate, xanthate, acetate and citrate starches. Other organic acids may also be used for the esterification:

formation of starch ethers
    starch alkyl ether, O-allyl ether, hydroxylalkyl ether, O-carboxylmethyl ether, N-containing starch ethers, P-containing starch ethers and S-containing starch ethers.

formation of branched starches
formation of starch graft polymers.

FIG. 1 schematically illustrates the plasmid pJT31 (AATP1 (*Arabidopsis thaliana*) sense);

FIG. 2 schematically illustrates the plasmid pJT32 (AATP1 (*Solanum tuberosum*) antisense);

FIG. 3 shows the comparison of the amino-acid sequence of the AATP2(SEQ ID NO:6) from *Arabidopsis thaliana* with the AATP1 (*A. thaliana*) (SEQ ID NO:5) and a homologous protein from *Rickettsia prowazekii* (SEQ ID NO:7) Williamson et al., Gene 80 (1989), 269–278);

FIG. 4 hydropathy analysis of AATP2 (*A. thaliana*), AATP1 (*A. thaliana*) and the *Rickettsia* ADP/ATP translocator carried out according to the method of von Heijne et al. (Eur. J. Biochem. 180 (1989), 535–545)

Figure 7:
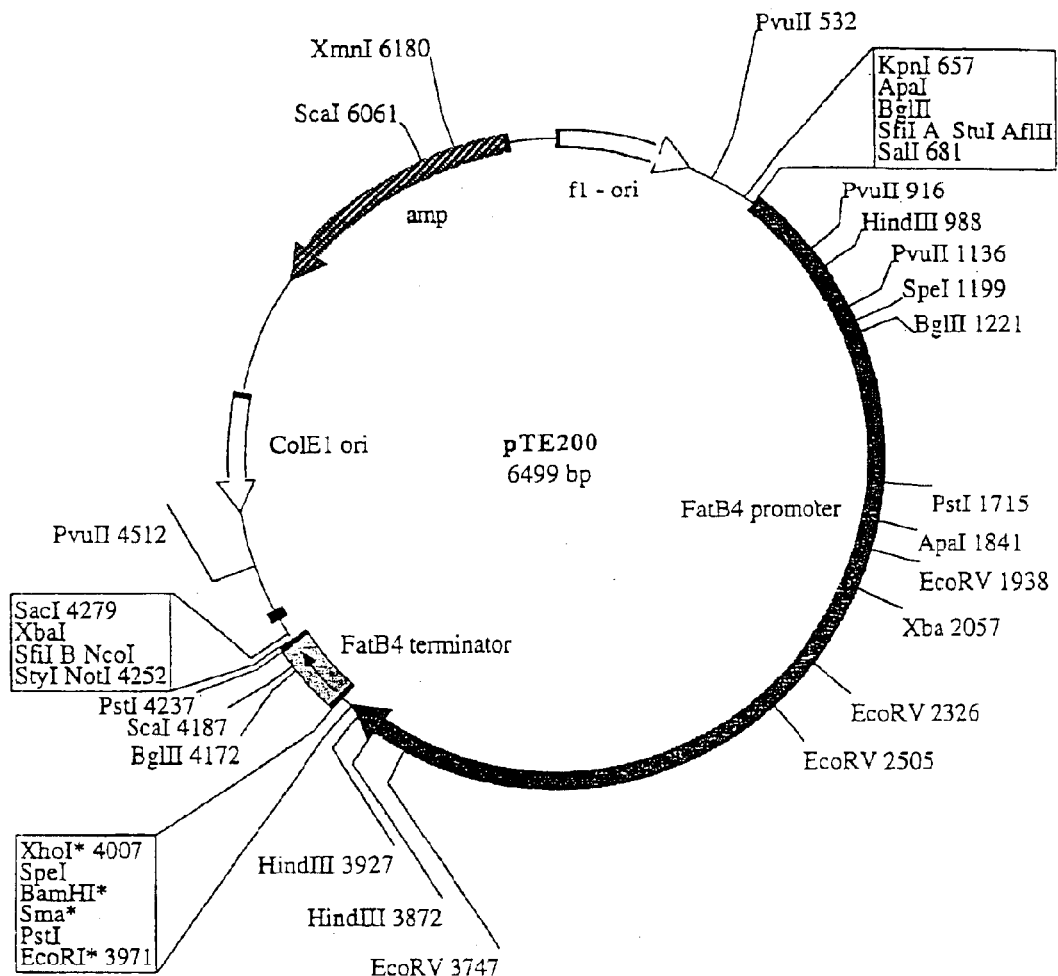

FIG. 7 Schematic map of the cassette pTE200 for the embryo-specific gene expression. EcoRI, SmaI, BamHI, XhoI, NotI, XbaI, SacI, KpnI, ApaI, SalI and SfiI mark recognition sites for restriction endonucleases. For practical reasons, SfiI (A) and SfiI (B) differ in the variable nucleotide sequence within the recognition sequence. The abbreviations encode as follows: PClFatB4=ClFatB4 promoter, tClFatB4=ClFatB4 terminator, amp=bacterial resistance against ampicillin, ColE1 ori="origin of replication" from the plasmid ColE1, f1(−) ori="origin of replication" from the phage f1.

Figure 8:
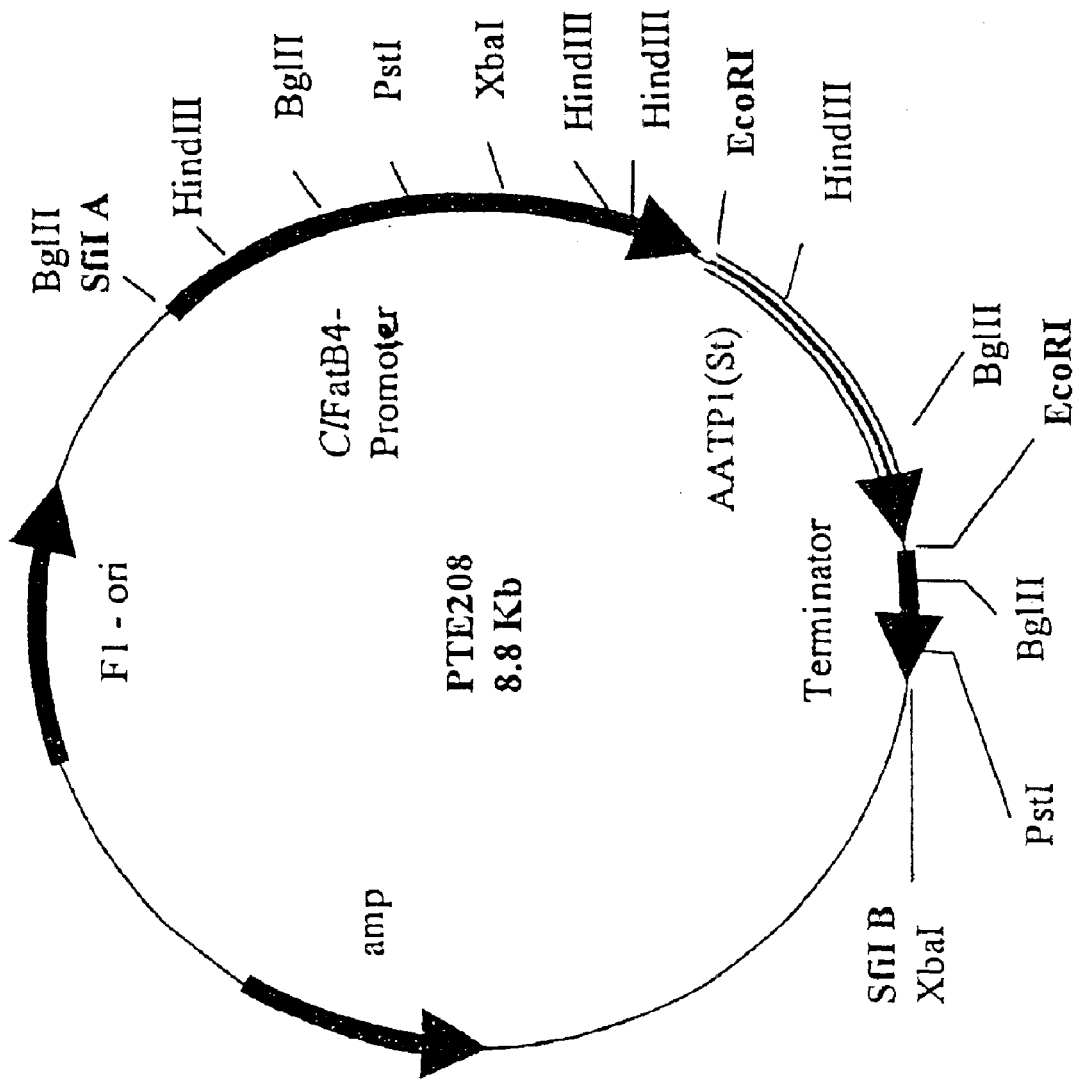

FIG. 8 Schematic map of the ADP/ATP translocator expression cassette pTE208: this derivative of the vector pTE200 (FIG. 7) carries a cDNA coding for a plastidial ADP/ATP translocator from Solanum tuberosum in sense-orientation.

Figure 9:
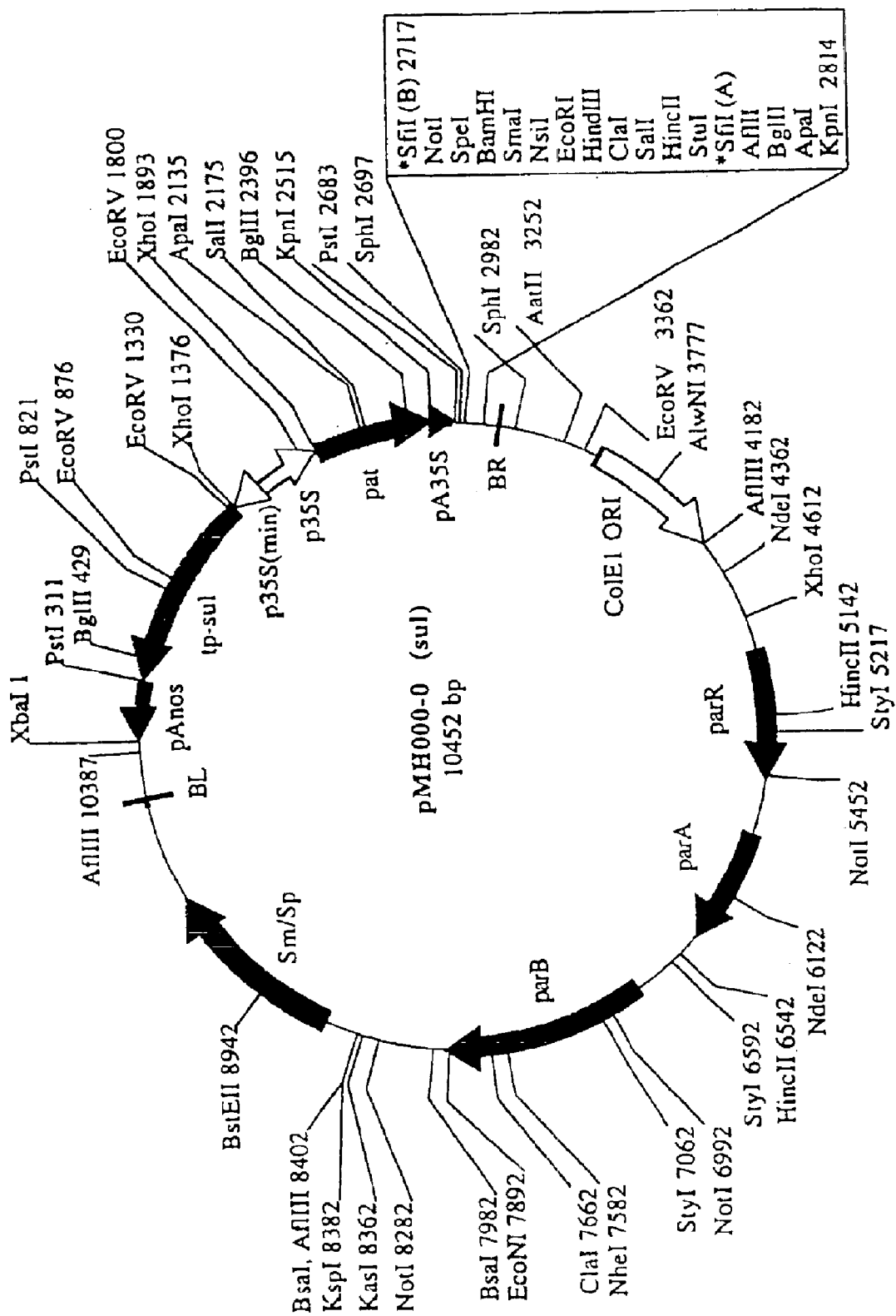

FIG. 9 Schematic map of the binary vector pMH000-0. SfiI, SalI, ClaI, HindIII, EcoRI, NsiI, SmaI, BamHI, SpeI, NotI, KpnI, BglII, ApaI, XhoI, XbaI and BstEII mark recognition sites for restriction endonucleases. SfiI (A) and SfiI (B) differ in the variable nucleotide sequence of their recognition sequence as stated. This is the reason why a recircularization of the starting plasmid is prevented after SfiI cleavage and a directed insertion of the expression cassette from the pTE200 derivative is possible. The abbreviations encode as follows: RB, LB=right and left border region, t35S—termination signal of the 35S rna gene from CaMV, pat=phophinotricin acetyl transferase gene, p35S=promoter of the 35S rna gene from CaMV, p35S(min)=minimal promoter of the 35S rna gene from CaMV, tp-sul=sulfonamid resistance gene with transit peptide, tnos=termination signal of the nopalin synthase gene, Sm/Sp=bacterial resistance against streptomycin and spectinomycin, parA, parB and parR=plasmid multiplication functions from the plasmid pVS1 with large host area i.a. for *Agrobacterium tumefaciens* and *Escherichia coli*.

The following examples illustrate the invention.

Example 1

Construction of the Bacterial Expression Vector pJT118 and Transformation of *E. coli*

The AATP2 protein (gene library X94626) from *Arabidopsis thaliana* was N-terminally fused with a "histidine-tag" comprising 10 aminos acids.

For this, the cDNA encoding the whole AATP2 protein from *Arabidopsis thaliana* was isolated by means of a PCR approach. The following oligonucleotide served as sense-primer which, in addition, had a XhoI-restriction site: cgtgagagatagagagctcgagggtctgattcaaacc (SEQ ID NO: 1); comprising the base pairs 66–102).

An oligonucleotide carrying an additional BamHI-restriction site served as antisense-primer gatacaacaggaatcctggatgaagc (SEQ ID NO: 2); comprising the base pairs 1863–1835). The obtained PCR product was purified by means of an agarose gel, cut with the restriction enzymes XhoI/BamHI and introduced "in frame" in the plasmid pET16b (Novagene, Heidelberg, Germany). This led to the exhibition of a histidine-tag of 10 amino acids at the N-terminus of the cDNA encoding the whole AATP2 protein from *Arabidopsis thaliana* (His-AATP2). Said vector was called pJT 118. The sequence of the PCR product was determined by sequencing of both nucleotide strands (Eurogentec). The transformation of *E. coli* C43 (Miroux and Walker, J. Mol. Biol. 260 (1996), 289–298) was carried out according to standard methods. The *E. coli* strain C43 allows for the heterologous expression of animal (Miroux and Walker, loc. cit.) and plant (Tjaden et al., J. Biol. Chem. (1998) (in press)) membrane proteins.

After transformation of said strain with the vector pJT118 uptake studies with radioactively marked ADP and ATP were carried out. It could be demonstrated by these studies that His-AATP2 can be functionally expressed in *E. coli* C43 in the cytoplasmic membrane of *E. coli*. This showed that AATP2 in fact encodes an ADP/ATP translocator. The presence of a N-terminal histidine-tag leads to an increase (2×–3×) of the transport activity of AATP2 from *A. thaliana* in *E. coli* in comparison with AATP2 without N-terminal his-tag.

Example 2

Figure 1:
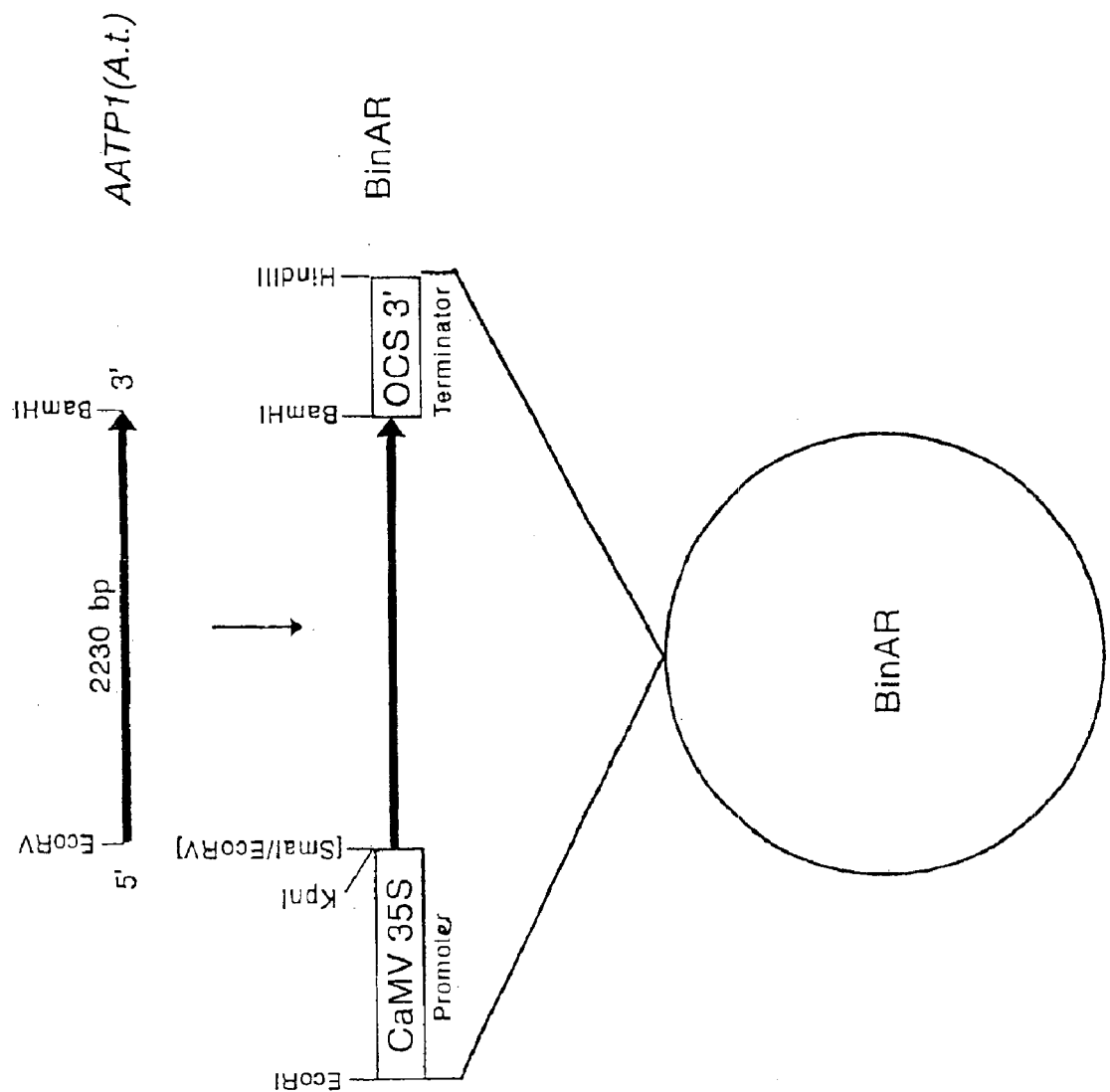

Construction of the Plasmid pJT31 and Introduction of the Plasmid into the Genome of Potato Plants For the construction of a plant transformation vector an EcoRV/BamHI fragment of the AATP1-cDNA from *A. thaliana* (Kampfenkel et al., FEBS Letters 374 (1995), 351–355) with a length of 2230 bp was ligated into the vector pBinAR cut with SmaI/EcoRV and BamHI (Höfgen and Willmitzer, Plant Sci. 66 (1990), 221–230). By insertion of the cDNA fragment an expression cassette is formed (pJT31) which is constructed of the fragments A, B and C as follows (see FIG. 1):

Fragment A (540 bp) contains the 35S promoter from the cauliflower mosaic virus. Fragment B contains, in addition to the flanking regions, the protein-encoding region of an ADP/ATP translocator from *A. thaliana* (AATP1). Said region was isolated as described above and fused in sense-orientation to the 35S promoter in pBinAR. Fragment C (215 bp) contains the polyadenylation signal of the octopine synthase gene from *Agrobacterium tumefaciens*.

The size of the plasmid pJT31 is approximately 14.2 kb.

Figure 6:
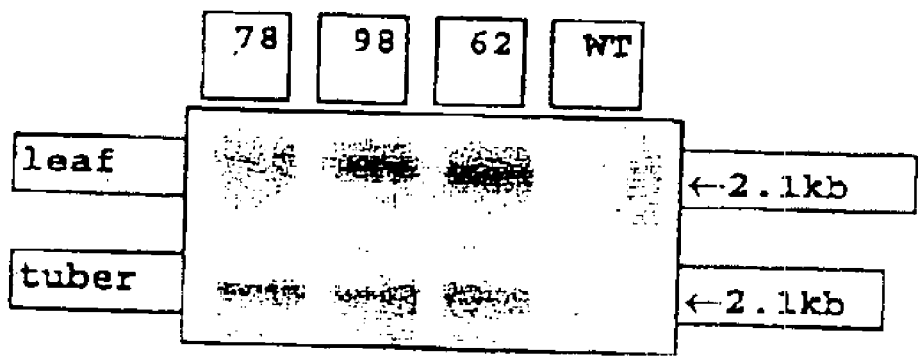
FIG. 6 shows a Northern blot analysis of the expression of the AATP1 (*Arabidopsis thaliana*) in leaf and tuber of ADP/ATP translocator overexpression plants.

The plasmid was transferred into potato plants by means of *Agrobacteria* as by Rocha-Sosa et al. (EMBO J. 8 (1989), 23–29). As a result of the transformation transgenic potato plants exhibited an increase of the mRNA of a plastidial ADP/ATP translocator. This was detected by Northern blot analysis (see FIG. 6). RNA was isolated according to standard protocols from leaf and tuber tissue from potato plants. 50 μg RNA were separated on an agarose gel (1.5% agarose, 1×MEN puffer, 16.6% formaldehyde). After electrophoresis the RNA was transferred with 20×SSC onto a nylon membrane Hybond N (Amersham, UK) by means of capillary blot. The RNA was fixed on the membrane by means of UV irradiation. The membrane was pre-hybridized for 2 hours in phosphate hybridization buffer (Sambrook et al., loc. cit.) and subsequently hybridized for 10 hours by means of addition of the radioactively labeled probe.

Example 3

Construction of the Plasmid pJT32 and Introduction of the Plasmid into the Genome of Potato Plants For the construction of a plant transformation vector a BamHI/NdeI fragment of the coding region of the AATP1-cDNA from *S. tuberosum* (Genbank Y10821) with a length of 1265 bp was ligated into the vector pBinAR (Höfgen and Willmitzer, Plant Sci. 66 (1990), 221–230) cut with SmaI/NdeI and BamHI.

Figure 2:
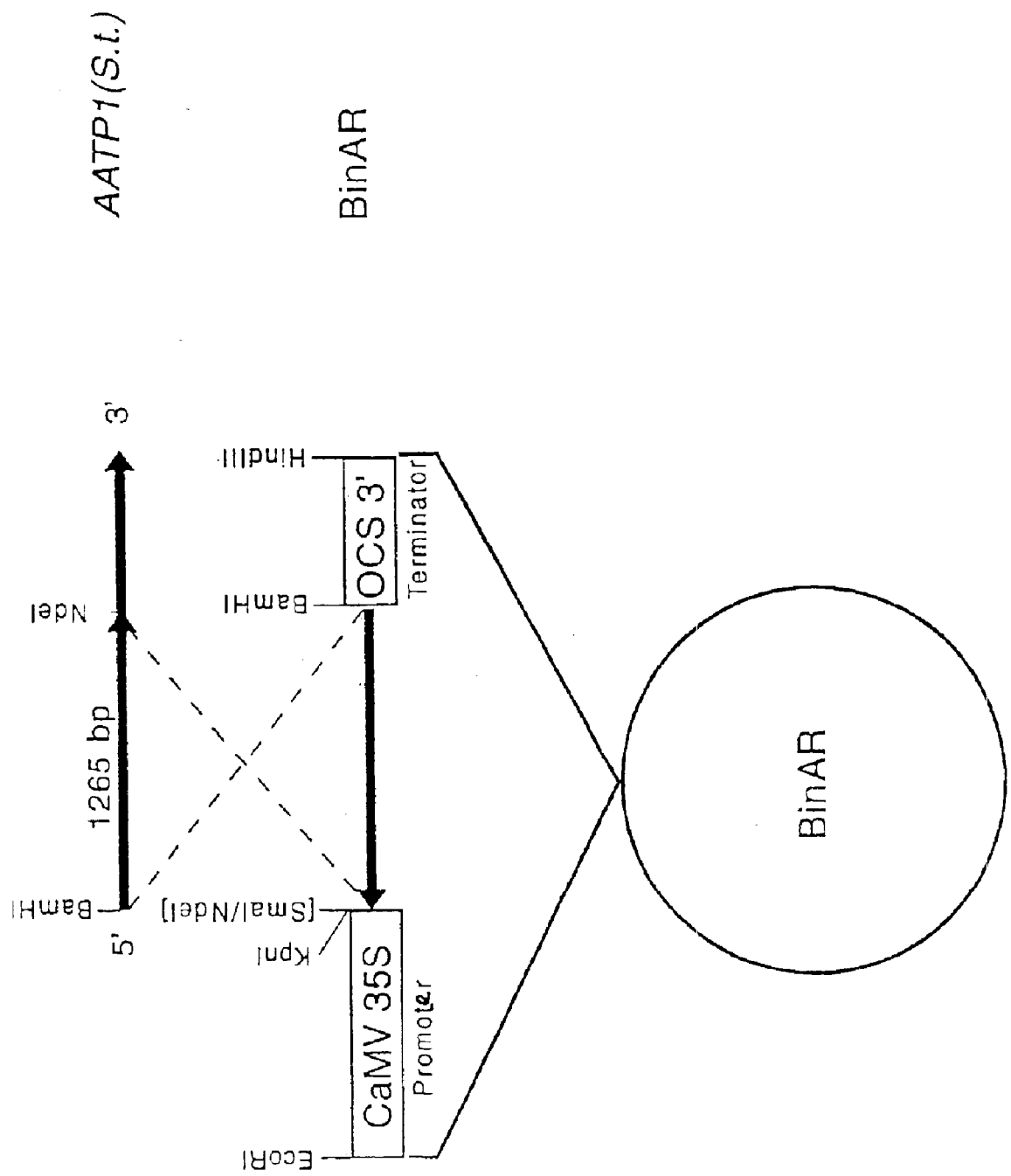
Figure 4:
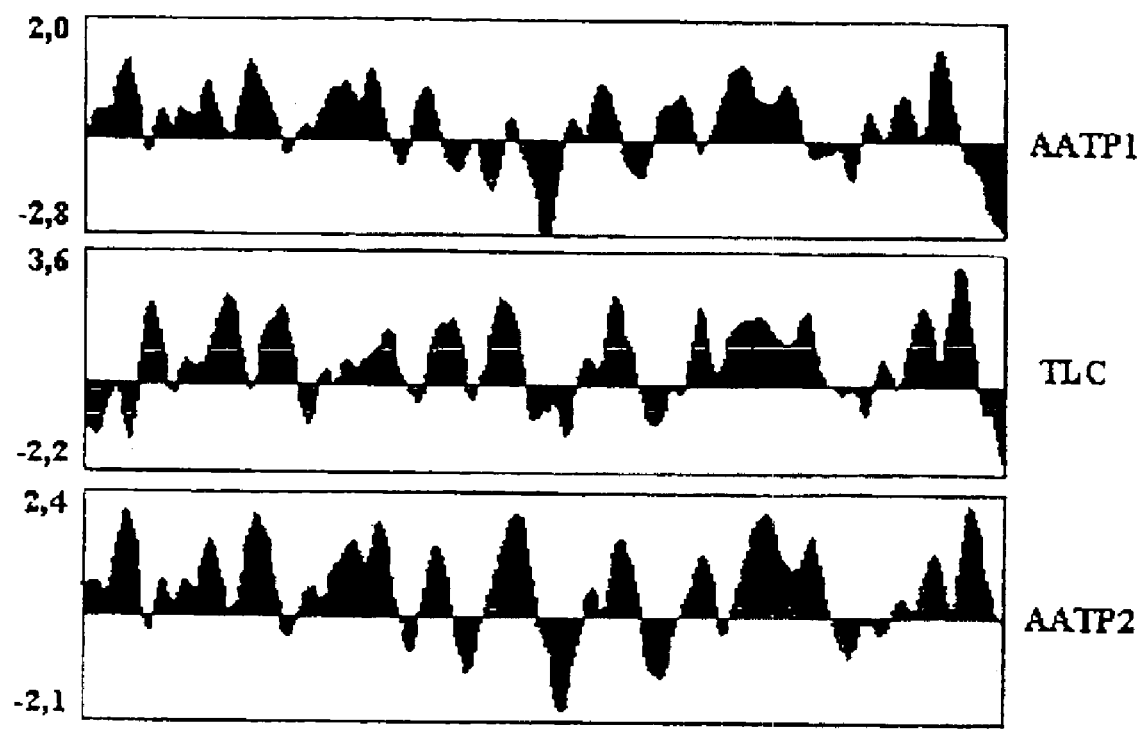

By insertion of the cDNA fragment an expression cassette is formed which is constructed of the fragments A, B and C as follows (see FIG. 2):

Fragment A (540 bp) contains the 35S promoter from the cauliflower mosaic virus. Fragment B contains contains a region of an ADP/ATP translocator from *S. tuberosum* (AATP1 S.t.) with a length of 1265 bp. This region was fused in antisense-orientation to the 35S promoter in pBinAR.

Fragment C (215 bp) contains the polyadenylation signal of the octopine synthase gene from *Agrobacterium tumefaciens*.

The size of the plasmid pJT32 is approximately 13.3 kb.

The plasmid was transferred into potato plants by means of *Agrobacteria* as by Rocha-Sosa et al. (EMBO J. 8 (1989), 23–29).

Figure 5:
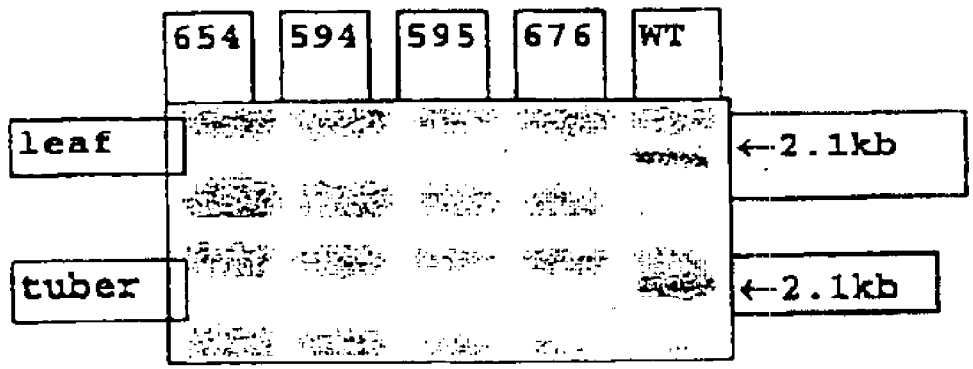
FIG. 5 shows a Northern blot analysis of the expression of the AATP1 (*Solanum tuberosum*) in leaf and tuber of ADP/ATP translocator antisense plants.

As a result of the transformation transgenic potato plants exhibited a decrease of the mRNA of a plastidial ADP/ATP translocator. This was detected by Northern blot analysis (see FIG. 5). RNA was isolated according to standard protocols from leaf and tuber tissue from potato plants. 50 μg RNA were separated on an agarose gel (1.5% agarose, 1×MEN puffer, 16.6% formaldehyde). After electrophoresis the RNA was transferred with 20×SSC onto a nylon membrane Hybond N (Amersham, UK) by means of capillary blot. The RNA was fixed on the membrane by means of UV irradiation. The membrane was pre-hybridized for 2 hours in phosphate hybridization buffer (Sambrook et al., loc. cit.) and subsequently hybridized for 10 hours by means of addition of the radioactively labeled probe.

Example 4

Analysis of the Starch, Amylose and Sugar content of Transgenic Potato Plants

The determination of the content of soluble sugars was carried as described by Lowry and Passonneau in "A Flexible System of Enzymatic Analysis", Academic Press, New York, USA (1972). The determination of the starch content was carried out as described by Batz et al. (Plant Physiol. 100 (1992), 184–190).

TABLE 1

| line/genotype | starch in (μmolC6units/g fresh weight) | soluble sugars in (μmol/g fresh weight) |
|---|---|---|
| Desiree/WT | 1094.0 | 26.49 |
| 654/antisense-AATP1 (*S. tuberosum*) | 574.2 | 42.52 |
| 594/antisense-AATP1 (*S. tuberosum*) | 630.2 | 48.76 |
| 595/antisense-AATP1 (*S. tuberosum*) | 531.4 | 45.92 |
| 676/antisense-AATP1 (*S. tuberosum*) | 883.0 | 40.60 |
| 62/sense-AATP1 (*A. thaliana*) | 1485.0 | 30.65 |
| 98/sense-AATP1 (*A. thaliana*) | 1269.0 | 18.28 |
| 78/sense-AATP1 (*A. thaliana*) | 995.0 | 20.50 |

The determination of the amylose content was carried out as described by Hovenkamp-Hermelink et al. (Potato Res. 31 (1988), 241–246):

| line/genotype | % amylose |
|---|---|
| Desiree/WT | 18.8 |
| 654/antisense-AATP1 (*S. tuberosum*) | 15.5 |
| 594/antisense-AATP1 (*S. tuberosum*) | 14.3 |
| 595/antisense-AATP1 (*S. tuberosum*) | 18.0 |
| 676/antisense-AATP1 (*S. tuberosum*) | 11.5 |
| 62/sense-AATP1 (*A. thaliana*) | 27.0 |
| 98/sense-AATP1 (*A. thaliana*) | 22.7 |
| 78/sense-AATP1 (*A. thaliana*) | 24.5 |

Example 5

Production of an Expression Cassette and Transformation of Rape Plants

The expression cassette pTE200 in a pBluescript derivative (Short et al., Nucl. Acid Res. 16, (1988), 7583–7600) carries the promoter and terminator sequences of the thioesterase gene CIFatB4 (GenBank accession: AJ131741) from *Cuphea lanceolata* and suitable polylinker sequences for the insertion of various useful genes. Peripheral SfiI recognition sites with non-compatible nucleotides in the variable recognition regions allow for a directed transfer of the whole expression cassette including the useful gene into the corresponding restriction sites of the binary plasmid vector pMH000-0, a further development of pLH9000 (Hausmann and Töpfer, (1999): $9^{th}$ chapter: "Entwicklung von Plasmid-Vektoren" in Bioengineering für Rapssorten nach Maβ, D. Brauer, G. Röbbelen and R. Töpfer (eds.), Vorträge für Planzenzüchtung, Volume 45, 155–172), and prevent recirculization of the DNA in the recipient vector.

For the production of the expression cassette pTE200, first, a SalI-BbvI fragment carrying a promoter with an approximate length of 3.3 kb was isolated from the genomic clone CITEg16 (WO95/07357) carrying the complete CIFatB4 gene from *C. lanceolata*. In order to achieve this, the BbvI restriction site at the 3'-end of the promoter was opened and modified in such a way that the fragment could then be taken up by the pBluescript (stratagene) cut with SalI and SmaI. An internal EcoR restriction site of the fragment located 1211 nucleotides 5' was deleted by being opened, modified by means of T4 polymerase and subsequently closed again.

The terminator sequence was amplified by means of the polymerase chain reaction and specific oligonucleotide primers at the CITEg16 matrix (WO95/07357) and provided with various polylinker restriction sites (MCS) via the primers. The sequences of the primers are: 5'GAATTCCT-GCAGCCCGGGGGATCCACTAGTCTC-GAGAAGTGGCTGGGGGCCT TTCC3' (SEQ ID NO: 3)=5'-primer: (MCS: EcoRI, PstI, SmaI, BamHI, SpeI XhoI; CIFatB4 terminator: from pos. 35–56) and 5'TCTAGAG-GCCAAGGCGGCCGCTTCAACGGACTGCAGTGC3' (SEQ ID NO: 4)=3'-primer CIFatB4 terminator: from pos. 22–39, MCS: NotI, StyI, SfiI, XbaI. The amplificate was cut with EcoRI and NotI and inserted into the corresponding restriction sites of the pBlueSfi BA (Hausmann and Töpfer, see above). The fragment carrying the promoter was opened with BamHI, modified and subsequently cut with SalI to place it in the pBlueSfi BA vector via SalI and modified HindIII restriction site in front of the terminator. The result is the expression cassette pTE200 (see FIG. 7). For the contruction of a plant transformation vector an EcoRI fragment of the AATP1 cDNA from *Solanum tuberosum* (pTM1, Tjaden et al., The Plant Journal 16 (1998) 531–540) with a length of 2270 bp was ligated into the vector pTE200 opened with EcoRI. The orientation was controlled by means of restriction digest. The result was the plasmid pTE208 (FIG. 8). In the following step, the SfiI fragment from pTE208 was inserted into the polylinker restriction sites of the binary vector pMH000-0 (FIG. 9) in a directed manner. The result was the vector pMH 0208.

The binary plasmid vector pMH000-0 has been developed further from pLH9000 (Hausmann and Töpfer, see above) with alternative selection markers for the plant transformation. The sulfonamide gene (sul) was isolated together with the signal peptide sequence (tp) for plastidial import of the small subunit of the ribulosebiphosphate carboxylase from the precursor plasmid of pS001 (Reiss et al., Proc. Natl. Acad. Sci. USA 93, (1996), 3094–3098) after modification of the Asp718-to the XhoI-restriction site. The XhoI-SalI fragment was inserted into the XhoI— and BamHI-restriction sites of a pBluescript derivative in front of the terminator of the nopalin synthase gene (pAnos) after modification of SalI and BamHI. In a subsequent three fragment ligation the resulting tpsul-pAnos fragment (XhoI-XbaI) and the XhoI-HindIII fragment from pRT103pat (Töpfer et al., Methods in Enzymol. 217, (1993), 66–78) were united with the plasmid pK18 (Pridmore, Gene 56, (1987), 309–312) opened by means of HindIII and XbaI. As a result the gene for the phosphinotricin acetyltransferase with the terminator of the CaMV35S rna gene from pRT103pat was placed in opposite orientation to the tpsul-pAnos unit. A dual promoter of the CaMV35S rna gene as XhoI fragment from a descendant of pROA93 (Ott et al., Mol. Gen. Genet. 221, (1990), 121–124) was inserted into the XhoI restriction site between the resistance-mediating gene sequences to complete said double selection unit (for resistance against the herbicide Basta and the sulfonamide sulfadiazin). After corresponding modifications in the adjacent polylinker the resulting dual selection cassette was exchanged by means of XbaI and HindIII against the kanamycin cassette in the pLH9000 precursor plasmid (Hausmann and Töpfer, see above). The result was the binary plasmid vector pMH000-0.

The transformation of hypocotyl explants of rape of the variety Drakkar was carried out according to the protocol of De Block (Plant Physiol. 91 (1989), 694–701) by means of *Agrobacteria* (strain GV 3101 C58C1 Rifr) carrying the binary vector pMH0208 (ATP/ADP transporter sense). Shoots were regenerated on selective nutrient medium (sulfonamide) and cultivated in the greenhouse up to seed maturation. By means of PCR and leaf test (tolerance against glufosinatammonium (Basta®)) it was tested which plants contained the transgene. Maturing embryos at various developmental stages were harvested from said plants and stored in liquid nitrogen.

For the determination of the oil content mature seeds of transgenic rape lines and of control lines were analysed by means of the non-invasive near infrared spectroscopy (described, for example, by Schulz et al., J. Near Infrared Spectrosc. 6, (1998), A125–A130; Starr et al., J. Agric. Sci. 104(2), (1985), 317–323).

What is claimed is:

1. A genetically modified plant cell wherein a foreign nucleic molecule encoding a plastidial ADP/ATP translocator is integrated into the nuclear genome of said genetically modified plant cell and wherein the expression of said foreign nucleic acid molecule results in an increase in plastidial ADP/ATP translocator activity in comparison with corresponding non-genetically modified plant cells from wild type plants.

2. The genetically modified plant cell according to claim 1 exhibiting an increased starch content in comparison with corresponding non-genetically modified plant cells.

3. The genetically modified plant cell according to claim 1 synthesizing a starch fraction exhibiting an increased amylose-content in comparison with a starch fraction from corresponding non-genetically modified plant cells.

4. A genetically modified plant containing transgenic plant cells according to claim 1.

5. The genetically modified plant according to claim 4, which is a maize, wheat or potato plant.

6. A method for the production of a transgenic plant exhibiting an increased yield in comparison with wild type plants, wherein
   (a) a plant cell is genetically modified by integrating a foreign nucleic acid molecule encoding a plastidial ADP/ATP translocator into the nuclear genome of said plant cell wherein the expression of said foreign nucleic acid molecule results in an increase in plastidial ADP/ATP translocator activity in the cell;
   (b) a plant is regenerated from the cell produced according to step (a); and
   (c) further transgenic plants are optionally produced from the plant produced according to step (b).

7. The method according to claim 6, wherein the transgenic plant exhibits (a) an increased starch content in comparison with wild type plants, (b) a starch fraction with an increased amylose content in comparison with a starch fraction from the wild type plants, or (c) both an increased starch content in comparison with wild type plants and a starch fraction with an increased amylose content in comparison with starch friction from wild type plants.

8. A transgenic plant obtainable by the method according to claim 6 or 7.

9. Propagation material of genetically modified plants according to any one of claim 4 or 5, wherein the propagation material has ADP/ATP translocator activity.

10. A method for the production of a modified starch comprising the extraction of the starch from a plant according to any one of claim 4 or 5.

11. The genetically modified plant cell according to claim 1 exhibiting an increased starch content in comparison with corresponding non-genetically modified plant cells.

12. The method according to claim 6, wherein the transgenic plant exhibits an increased starch content in comparison with wild type plants and a starch fraction with an increased amylose content in comparison with a starch fraction from wild type plants.

13. The method according to claim 6, wherein the transgenic plant exhibits an increased starch content in comparison with wild type plants or a starch fraction with an increased amylose content in comparison with a starch fraction from wild type plants.

14. A transgenic plant produced by the method according to claim 6.

15. A genetically modified plant cell wherein a foreign nucleic molecule encoding an *Arabidopsis thaliana, Solanum tuberosum, Rickettsia prowazekii* or *Chlamydia*

*trachomatis* plastidial ADP/ATP translocator is integrated into the nuclear genome of said genetically modified plant cell and wherein the expression of said foreign nucleic acid molecule results in an increase in plastidial ADP/ATP translocator activity in comparison with corresponding non-genetically modified plant cells from wild type plants.

16. A genetically modified plant cell wherein a foreign nucleic molecule encoding a plastidial ADP/ATP translocator protein having an amino acid sequences of SEQ ID NO. 5, SEQ ID NO. 6 or SEQ ID NO. 7 is integrated into the nuclear genome of said genetically modified plant cell and wherein the expression of said foreign nucleic acid molecule results in an increase in plastidial ADP/ATP translocator activity in comparison with corresponding non-genetically modified plant cells from wild type plants.

17. A method for the production of a transgenic plant exhibiting an increased starch, increased amylose, or increased starch and amylose in comparison with wild type plants, wherein
   (a) a plant cell is genetically modified by integrating a foreign nucleic acid molecule encoding an *Arabidopsis thaliana, Solanum tuberosum, Rickettsia prowazekii* or *Chlamydia trachomatis* plastidial ADP/ATP translocator into the nuclear genome of said plant cell wherein the expression of said foreign nucleic acid molecule results in an increase in plastidial ADP/ATP locator activity in the cell;
   (b) a plant is regenerated from the cell produced according to step (a); and
   (c) further transgenic plants are optionally produced from the plant produced according to step (b).

18. A method for the production of a transgenic plant exhibiting an increased starch, increased amylose, or increased starch and amylose in comparison with wild type plants, wherein
   (a) a plant cell is genetically modified by integrating a foreign nucleic acid molecule encoding a plastidial ADP/ATP translocator protein having an amino acid sequence of SEQ ID NO. 5, SEQ ID NO. 6 or SEQ ID NO. 7 into the nuclear genome of said plant cell wherein the expression of said foreign nucleic acid molecule results in an increase in plastidial ADP/ATP translocator activity in the cell;
   (b) a plant is regenerated from the cell produced according to step (a); and
   (c) further transgenic plants are optionally produced from the plant produced according to step (b).

19. A method for the production of a transgenic plant exhibiting an increased starch, increased amylose, or increased starch and amylose in comparison with wild type plants, wherein
   (a) a plant cell is genetically modified by integrating a foreign nucleic acid molecule encoding a plastidial ADP/ATP translocator protein whose amino acid sequence is at least 66% homologous to SEQ ID NO. 5 into the nuclear genome of said plant cell wherein the expression of said foreign nucleic acid molecule results in an increase in plastidial ADP/ATP translocator activity in the cell;
   (b) a plant is regenerated from the cell produced according to step (a); and
   (c) further transgenic plants are optionally produced from the plant produced according to step (b).

20. A genetically modified plant cell wherein a foreign nucleic molecule encoding a plastidial ADP/ATP translocator protein whose amino acid sequence is at least 66% homologous to SEQ ID NO. 5 is integrated into the nuclear genome of said genetically modified plant cell and wherein the expression of said foreign nucleic acid molecule results in an increase in plastidial ADP/ATP translocator activity in comparison with corresponding non-genetically modified plant cells from wild type plants.

* * * * *

SEQUENCE LISTING

```
<160> NUMBER OF SEQ ID NOS: 7

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence:
      sense-primer

<400> SEQUENCE: 1
cgtgagagat agagagctcg agggtctgat tcaaacc                              37

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:
      antisense-primer

<400> SEQUENCE: 2
gatacaacag gaatcctgga tgaagc                                          26

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 3
```

```
gaattcctgc agcccggggg atccactagt ctcgagaagt ggctgggggc ctttcc        56
```

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 4

```
tctagaggcc aaggcggccg cttcaacgga ctgcagtgc                           39
```

<210> SEQ ID NO 5
<211> LENGTH: 589
<212> TYPE: PRT
<213> ORGANISM: Arabidopsis thaliana

<400> SEQUENCE: 5

```
Met Glu Ala Val Ile Gln Thr Arg Gly Leu Leu Ser Leu Pro Thr Lys
  1               5                  10                  15

Pro Ile Gly Val Arg Ser Gln Leu Gln Pro Ser His Gly Leu Lys Gln
             20                  25                  30

Arg Leu Phe Ala Ala Lys Pro Arg Asn Leu His Gly Cys Leu Tyr Pro
         35                  40                  45

Leu Thr Gly Thr Arg Asn Phe Lys Pro Leu Ser Gln Pro Cys Met Gly
     50                  55                  60

Phe Arg Phe Pro Thr Lys Arg Glu Ala Pro Ser Ser Tyr Ala Arg Arg
 65                  70                  75                  80

Arg Arg Gly Cys Trp Arg Arg Ser Cys Leu Arg Arg Ser Asp Ser Ala
                 85                  90                  95

Ala Val Ala Ser Arg Lys Ile Phe Gly Val Glu Val Ala Thr Leu
            100                 105                 110

Lys Lys Ile Ile Pro Leu Gly Leu Met Phe Phe Cys Ile Leu Phe Asn
        115                 120                 125

Tyr Thr Ile Leu Arg Asp Thr Lys Asp Val Leu Val Val Thr Ala Lys
    130                 135                 140

Gly Ser Ser Ala Glu Ile Ile Pro Phe Leu Lys Thr Trp Val Asn Leu
145                 150                 155                 160

Pro Met Ala Ile Gly Phe Met Leu Leu Tyr Thr Lys Leu Ser Asn Val
                165                 170                 175

Leu Ser Lys Lys Ala Leu Phe Tyr Thr Val Ile Val Pro Phe Ile Ile
            180                 185                 190

Tyr Phe Gly Gly Phe Gly Phe Val Met Tyr Pro Leu Ser Asn Tyr Ile
        195                 200                 205

His Pro Glu Ala Leu Ala Asp Lys Leu Leu Thr Thr Leu Gly Pro Arg
    210                 215                 220

Phe Met Gly Pro Ile Ala Ile Leu Arg Ile Trp Ser Phe Cys Leu Phe
225                 230                 235                 240

Tyr Val Met Ala Glu Leu Trp Gly Ser Val Val Ser Val Leu Phe
                245                 250                 255

Trp Gly Phe Ala Asn Gln Ile Thr Thr Val Asp Glu Ala Lys Lys Phe
            260                 265                 270

Tyr Pro Leu Phe Gly Ile Gly Ala Asn Val Ala Leu Ile Phe Ser Gly
        275                 280                 285

Arg Thr Val Lys Tyr Phe Ser Asn Leu Arg Lys Asn Leu Gly Pro Gly
    290                 295                 300
```

```
Val Asp Gly Ser Phe Val Glu Ser His Asp Glu His Cys Gly Gly Asn
305                 310                 315                 320

Gly Thr Arg Ile Cys Leu Ser Ile Gly Gly Ser Asn Arg Tyr Val Pro
                325                 330                 335

Leu Pro Thr Arg Ser Lys Asn Lys Lys Glu Lys Pro Lys Met Gly Thr
                340                 345                 350

Met Glu Ser Leu Lys Phe Leu Val Ser Ser Pro Tyr Ile Arg Asp Leu
            355                 360                 365

Ala Thr Leu Val Val Ala Tyr Gly Ile Ser Ile Asn Leu Val Glu Val
        370                 375                 380

Thr Trp Lys Ser Lys Leu Lys Ala Gln Phe Pro Ser Pro Asn Glu Tyr
385                 390                 395                 400

Ser Ala Phe Met Gly Ala Phe Ser Thr Cys Thr Gly Val Ala Thr Phe
                405                 410                 415

Thr Met Met Leu Leu Ser Gln Tyr Val Phe Asn Lys Tyr Gly Trp Gly
                420                 425                 430

Val Ala Ala Lys Ile Thr Pro Thr Val Leu Leu Thr Gly Val Ala
            435                 440                 445

Phe Phe Ser Leu Ile Leu Phe Gly Gly Pro Phe Ala Pro Leu Val Ala
        450                 455                 460

Lys Leu Gly Met Thr Pro Leu Ala Ala Val Tyr Val Gly Ala Leu
465                 470                 475                 480

Gln Asn Ile Phe Ser Lys Ser Ala Lys Tyr Ser Leu Phe Asp Pro Cys
                485                 490                 495

Lys Glu Met Ala Tyr Ile Pro Leu Asp Glu Asp Thr Lys Val Lys Gly
            500                 505                 510

Lys Ala Ala Ile Asp Val Val Cys Asn Pro Leu Gly Lys Ser Gly Gly
        515                 520                 525

Ala Leu Ile Gln Gln Phe Met Ile Leu Ser Phe Gly Ser Leu Ala Asn
        530                 535                 540

Ser Thr Pro Tyr Leu Gly Met Ile Leu Val Ile Val Thr Ala Trp
545                 550                 555                 560

Leu Ala Ala Ala Lys Ser Leu Glu Gly Gln Phe Asn Ser Leu Arg Leu
                565                 570                 575

Lys Lys Ser Leu Arg Arg Lys Trp Arg Glu Leu His Arg
            580                 585

<210> SEQ ID NO 6
<211> LENGTH: 569
<212> TYPE: PRT
<213> ORGANISM: Arabidopsis thaliana

<400> SEQUENCE: 6

Met Glu Gly Leu Ile Gln Thr Arg Gly Ile Leu Ser Leu Pro Ala Ser
 1               5                  10                  15

His Arg Ser Glu Lys Val Leu Gln Pro Ser His Gly Leu Lys Gln Arg
                20                  25                  30

Leu Phe Thr Thr Asn Leu Pro Ala Leu Ser Leu Ser Leu Met Val Thr
            35                  40                  45

Arg Asn Phe Lys Pro Phe Ser Lys Ser His Leu Gly Phe Arg Phe Pro
        50                  55                  60

Thr Arg Arg Glu Ala Glu Asp Ser Leu Ala Arg Arg Lys Leu Arg Arg
65                  70                  75                  80

Pro Arg Arg Lys Cys Val Asp Glu Gly Asp Thr Ala Ala Met Ala Val
```

-continued

```
                85                  90                  95
Ser Pro Lys Ile Phe Gly Val Glu Val Thr Thr Leu Lys Lys Ile Val
            100                 105                 110
Pro Leu Gly Leu Met Phe Phe Cys Ile Leu Phe Asn Tyr Thr Ile Leu
            115                 120                 125
Arg Asp Thr Lys Asp Val Leu Val Thr Ala Lys Gly Ser Ser Ala
            130                 135                 140
Glu Ile Ile Pro Phe Leu Lys Thr Trp Val Asn Val Pro Met Ala Ile
145                 150                 155                 160
Gly Phe Met Leu Leu Tyr Thr Lys Leu Ser Asn Val Leu Ser Lys Lys
                165                 170                 175
Ala Leu Phe Tyr Thr Val Ile Val Pro Phe Ile Val Tyr Phe Gly Ala
            180                 185                 190
Phe Gly Phe Val Met Tyr Pro Arg Ser Asn Leu Ile Gln Pro Glu Ala
            195                 200                 205
Leu Ala Asp Lys Leu Leu Ala Thr Leu Gly Pro Arg Phe Met Gly Pro
            210                 215                 220
Leu Ala Ile Met Arg Ile Trp Ser Phe Cys Leu Phe Tyr Val Met Ala
225                 230                 235                 240
Glu Leu Trp Gly Ser Val Val Ser Val Leu Phe Trp Gly Phe Ala
                245                 250                 255
Asn Gln Ile Thr Thr Val Asp Glu Ala Lys Lys Phe Tyr Pro Leu Phe
                260                 265                 270
Gly Leu Gly Ala Asn Val Ala Leu Ile Phe Ser Gly Arg Thr Val Lys
                275                 280                 285
Tyr Phe Ser Asn Met Arg Lys Asn Leu Gly Pro Gly Val Asp Gly Trp
            290                 295                 300
Ala Val Ser Leu Lys Ala Met Met Ser Ile Val Val Gly Met Gly Leu
305                 310                 315                 320
Ala Ile Cys Phe Leu Tyr Trp Trp Val Asn Arg Tyr Val Pro Leu Pro
                325                 330                 335
Thr Arg Ser Lys Lys Lys Val Lys Pro Gln Met Gly Thr Met Glu
            340                 345                 350
Ser Leu Lys Phe Leu Val Ser Ser Pro Tyr Ile Arg Asp Leu Ala Thr
            355                 360                 365
Leu Val Val Ala Tyr Gly Ile Ser Ile Asn Leu Val Glu Val Thr Trp
            370                 375                 380
Lys Ser Lys Leu Lys Ser Gln Phe Pro Ser Pro Asn Glu Tyr Ser Ala
385                 390                 395                 400
Phe Met Gly Asp Phe Ser Thr Cys Thr Gly Ile Ala Thr Phe Thr Met
                405                 410                 415
Met Leu Leu Ser Gln Tyr Val Phe Lys Lys Tyr Gly Trp Gly Val Ala
            420                 425                 430
Ala Lys Ile Thr Pro Thr Val Leu Leu Thr Gly Val Ala Phe Phe
            435                 440                 445
Ser Leu Ile Leu Phe Gly Gly Pro Phe Ala Pro Leu Ala Lys Leu
            450                 455                 460
Gly Met Thr Pro Leu Leu Ala Ala Val Tyr Val Val Pro Glu Val
465                 470                 475                 480
Ser Ser Ala Arg Val Gln Val Gln His Ser Ser Thr Pro Ser Ala Met
            485                 490                 495
Gln Glu Cys Leu Tyr Pro Leu Asp Glu Val Ser Lys Val Lys Ala Lys
            500                 505                 510
```

```
Leu Gln Leu Met Trp Ser Ala Thr Ile Gly Lys Ser Gly Gly Ala Leu
        515                 520                 525

Ile Gln Gln Phe Met Ile Leu Thr Phe Gly Ser Leu Ala Asn Ser Thr
    530                 535                 540

Pro Tyr Leu Gly Val Ile Leu Leu Gly Ile Val Thr Ala Trp Leu Ala
545                 550                 555                 560

Ala Ala Lys Ser Leu Glu Gly Pro Val
                565

<210> SEQ ID NO 7
<211> LENGTH: 498
<212> TYPE: PRT
<213> ORGANISM: Rickettsia prowazekii

<400> SEQUENCE: 7

Met Ser Thr Ser Lys Ser Glu Asn Tyr Leu Ser Glu Leu Arg Lys Ile
1               5                   10                  15

Ile Trp Pro Ile Glu Gln Tyr Glu Asn Lys Lys Phe Leu Pro Leu Ala
            20                  25                  30

Phe Met Met Phe Cys Ile Leu Leu Asn Tyr Ser Thr Leu Arg Ser Ile
        35                  40                  45

Lys Asp Gly Phe Val Val Thr Asp Ile Gly Thr Glu Ser Ile Ser Phe
    50                  55                  60

Leu Lys Thr Tyr Ile Val Leu Pro Ser Ala Val Ile Ala Met Ile Ile
65                  70                  75                  80

Tyr Val Lys Leu Cys Asp Ile Leu Lys Gln Glu Asn Val Phe Tyr Val
                85                  90                  95

Ile Thr Ser Phe Phe Leu Gly Tyr Phe Ala Leu Phe Ala Phe Val Leu
            100                 105                 110

Tyr Pro Tyr Pro Asp Leu Val His Pro Asp His Lys Thr Ile Glu Ser
        115                 120                 125

Leu Ser Leu Ala Tyr Pro Asn Phe Lys Trp Phe Ile Lys Ile Val Gly
    130                 135                 140

Lys Trp Ser Phe Ala Ser Phe Tyr Thr Ile Ala Glu Leu Trp Gly Thr
145                 150                 155                 160

Met Met Leu Ser Leu Leu Phe Trp Gln Phe Ala Asn Gln Ile Thr Lys
                165                 170                 175

Ile Ala Glu Ala Lys Arg Phe Tyr Ser Met Phe Gly Leu Leu Ala Asn
            180                 185                 190

Leu Ala Leu Pro Val Thr Ser Val Val Ile Gly Tyr Phe Leu His Glu
        195                 200                 205

Lys Thr Gln Ile Val Ala Glu His Leu Lys Phe Val Pro Leu Phe Val
    210                 215                 220

Ile Met Ile Thr Ser Ser Phe Leu Ile Ile Leu Thr Tyr Arg Trp Met
225                 230                 235                 240

Asn Lys Asn Val Leu Thr Asp Pro Arg Leu Tyr Asp Pro Ala Leu Val
                245                 250                 255

Lys Glu Lys Lys Thr Lys Ala Lys Leu Ser Phe Ile Glu Ser Leu Lys
            260                 265                 270

Met Ile Phe Thr Ser Lys Tyr Val Gly Tyr Ile Ala Leu Leu Ile Ile
        275                 280                 285

Ala Tyr Gly Val Ser Val Asn Leu Val Glu Gly Val Trp Lys Ser Lys
    290                 295                 300

Val Lys Glu Leu Tyr Pro Thr Lys Glu Ala Tyr Thr Ile Tyr Met Gly
```

-continued

```
              305                 310                 315                 320
Gln Phe Gln Phe Tyr Gln Gly Trp Val Ala Ile Ala Phe Met Leu Ile
                    325                 330                 335

Gly Ser Asn Ile Leu Arg Lys Val Ser Trp Leu Thr Ala Ala Met Ile
                340                 345                 350

Thr Pro Leu Met Met Phe Ile Thr Gly Ala Ala Phe Phe Ser Phe Ile
            355                 360                 365

Phe Phe Asp Ser Val Ile Ala Met Asn Leu Thr Gly Ile Leu Ala Ser
        370                 375                 380

Ser Pro Leu Thr Leu Ala Val Met Ile Gly Met Ile Gln Asn Val Leu
385                 390                 395                 400

Ser Lys Gly Val Lys Tyr Ser Leu Phe Asp Ala Thr Lys Asn Met Ala
                405                 410                 415

Tyr Ile Pro Leu Asp Lys Asp Leu Arg Val Lys Gly Gln Ala Ala Val
                420                 425                 430

Glu Val Ile Gly Gly Arg Leu Gly Lys Ser Gly Gly Ala Ile Ile Gln
            435                 440                 445

Ser Thr Phe Phe Ile Leu Phe Pro Val Phe Gly Phe Ile Glu Ala Thr
        450                 455                 460

Pro Tyr Phe Ala Ser Ile Phe Phe Ile Ile Val Ile Leu Trp Ile Phe
465                 470                 475                 480

Ala Val Lys Gly Leu Asn Lys Glu Tyr Gln Val Leu Val Asn Lys Asn
                485                 490                 495

Glu Lys
```